(12) United States Patent
Palumbo

(10) Patent No.: US 10,416,358 B2
(45) Date of Patent: Sep. 17, 2019

(54) DEVICE FOR REMOVING ENERGY FROM A BEAM AND A METHOD(S) OF USE THEREOF

(71) Applicants: TINTOMETER, GMBH, Dortmund (DE); Perry Palumbo, Fort Collins, CO (US)

(72) Inventor: Perry Palumbo, Fort Collins, CO (US)

( * ) Notice: Subject to any disclaimer, the term of this patent is extended or adjusted under 35 U.S.C. 154(b) by 254 days.

(21) Appl. No.: 15/511,154

(22) PCT Filed: Oct. 20, 2016

(86) PCT No.: PCT/US2016/057852
§ 371 (c)(1),
(2) Date: Mar. 14, 2017

(87) PCT Pub. No.: WO2017/070308
PCT Pub. Date: Apr. 27, 2017

(65) Prior Publication Data
US 2017/0248740 A1    Aug. 31, 2017

Related U.S. Application Data

(60) Provisional application No. 62/315,298, filed on Mar. 30, 2016, provisional application No. 62/244,004, filed on Oct. 20, 2015.

(51) Int. Cl.
*G02B 5/00* (2006.01)
*G01N 15/06* (2006.01)
(Continued)

(52) U.S. Cl.
CPC ............ *G02B 5/003* (2013.01); *G01J 1/0214* (2013.01); *G01J 1/0407* (2013.01); *G01N 15/06* (2013.01);
(Continued)

(58) Field of Classification Search
CPC ...... G02B 5/003; G01J 1/0214; G01J 1/0407; G01N 15/06; G01N 21/17; G01N 21/53;
(Continued)

(56) References Cited

U.S. PATENT DOCUMENTS 5,745,293 A    4/1998  Lassalle
5,835,231 A *  11/1998 Pipino ...................... G01J 3/42
                                                            356/440
(Continued)

FOREIGN PATENT DOCUMENTS

EP        0411907        6/1997

*Primary Examiner* — Georgia Y Epps
*Assistant Examiner* — Don J Williams
(74) *Attorney, Agent, or Firm* — Leyendecker & Lemire, LLC

(57) ABSTRACT

Embodiments of the present invention include a device for removing energy from a beam of electromagnetic radiation. Typically, the device can be operatively coupled to a turbidity measuring device to remove energy generated by the turbidity measuring device. The device can include a block of material having one of a plurality of different shapes coated in an energy absorbing material. Generally, the device can include an angled or rounded energy absorbing surface where the beam of electromagnetic radiation can be directed. The angled or rounded energy absorbing surface can configured to deflect a portion of the beam of electromagnetic radiation to a second energy absorbing surface.

13 Claims, 28 Drawing Sheets

(51) Int. Cl.
   *G01J 1/04* (2006.01)
   *G01J 1/02* (2006.01)
   *G01N 21/53* (2006.01)
   *G01N 21/17* (2006.01)
   *G01N 21/64* (2006.01)
   *G01N 21/85* (2006.01)

(52) U.S. Cl.
   CPC ............. *G01N 21/17* (2013.01); *G01N 21/53* (2013.01); *G01N 21/64* (2013.01); *G01N 21/85* (2013.01); *G01N 2015/0687* (2013.01); *G01N 2015/0693* (2013.01); *G01N 2201/0642* (2013.01)

(58) Field of Classification Search
   CPC ................... G01N 21/64; G01N 21/85; G01N 2015/0693; G01N 2015/0687; G01N 2201/0642
   See application file for complete search history.

(56) References Cited

U.S. PATENT DOCUMENTS

| | | |
|---|---|---|
| 7,293,886 B2 | 11/2007 | Holmgren et al. |
| 7,659,980 B1 | 2/2010 | Mitchell et al. |
| 2003/0210465 A1 | 11/2003 | Valenti |
| 2011/0284765 A1 | 11/2011 | Pieper et al. |

* cited by examiner

DEVICE FOR REMOVING ENERGY FROM A BEAM AND A METHOD(S) OF USE THEREOF

CROSS-REFERENCE TO RELATED APPLICATION

This application claims the benefit of U.S. Provisional Application No. 62/244,004, filed Oct. 20, 2015 and U.S. Provisional Application No. 62/315,298, filed Mar. 30, 2016.

FIELD OF THE INVENTION

Optics applicable to optical power measurement, electromagnetic beam measurement, and power control thereof.

BACKGROUND

A variety of devices have been disclosed in the past to dissipate a beam of energy. Previous devices include energy traps, light traps, beam dumps, and the like. All of the prior art devices have suffered from one or more drawbacks that made their use and performance less than ideal or desirable under at least certain circumstances.

An energy beam (e.g., a beam of light) is useful for the interrogation of properties or constituents of a liquid sample. Examples of properties of a liquid sample which can be interrogated by a beam of light include, but are not limited to, an amount of particulate matter present in the liquid correlated to an intensity of scattered, the absorption coefficient, pH, a chemical composition, a refractive index, a concentration of a chemical constituent comprising the liquid, and a density or temperature of the liquid.

In performing testing to ascertain the foregoing properties, it is common that the liquid to be measured is in equilibrium, and/or saturated, with a gas. For instance, the liquid can be in equilibrium with air for a given temperature and pressure. As an example, the liquid is saturated with gasses present in the environmental conditions at which the liquid is measured. It is also often advantageous for the detector used for the assay (or interrogation) of a liquid to be immersed in the sample within a measurement chamber and in close proximity to an energy beam so as to minimize signal loss and/or increase the energy density at the detector. It is therefore common for a light/energy trap to be integral with the measurement chamber to absorb the portion of the beam energy propagating outside the field of view of the detector (or more specifically a photodetector wherein the energy beam comprises light). The integral nature of the light trap often precludes replacement or interchangeability as may be desired for enhanced performance or other special requirements such as the assay of caustic liquids or other liquids that exceed typical operational parameters of the as-installed trap.

Most typically, the portions of an energy beam impingent upon an energy absorbing surface in a light/energy trap immersed in a liquid are absorbed and converted into heat. Localized heating of a liquid that is at equilibrium with a gas at a given temperature and pressure will cause localized outgassing of the liquid, precipitating the formation of gas bubbles on the impingent surface. The gas bubbles on the submerged surface of the trap increase reflectivity proximate the surface by (i) creating an additional optical interface (gas-liquid interface) between the liquid and each gas bubble, and (ii) increasing the difference in the refractive indices at the surface of the energy absorbing media (a gas-surface interface).

To further deleterious effect, bubbles disposed upon the immersed surface change the scatter characteristics of the surface by increasing the roughness of the apparent surface. As a result, an energy beam incident on such a surface will scatter light with greater intensity and with less predictability than a surface without bubbles. An increase in both the amount and direction of scattered energy increases the probability that at least some of this errant energy will be received by the detector. Errant energy received by the detector mimics the presence of analyte in the liquid and limits the detection thereof.

In applications where the excitation or interrogating energy beam does not terminate incident upon a detection means, such as in a turbidity or photoluminescence assay, even a small amount of stray energy can have significant negative effects on the accuracy of an assay. In a turbidity or a photoluminescence assay, the detector is commonly positioned at a right angle to the interrogating energy beam and the emissions from the analyte of interest are extremely weak (typically more than 10,000 times weaker than the energy of the interrogating beam). The high energy of the interrogating beam relative to the weak emissions of the analyte require high amplification of the emission response of the detection means making the detection means highly susceptible to stray energy of the excitation or interrogating beam.

The construction of prior art beam dump and energy/light trap devices also require the energy absorbing surfaces be compatible with the liquid in which they are immersed so that the low reflectance surface of the energy/light trap does not degrade over time and become more reflective causing drift and error in the measurement due to stray light as previously described. As can be appreciated, this constraint limits the number of materials available to manufacture an energy/light trap.

As a further drawback, at least some prior art energy/light trap devices are constructed integral to a measurement chamber which slows the response of the measurement chamber by placing obstructions along the flow path of a liquid sample.

DETAILED DESCRIPTION

Figure 1:
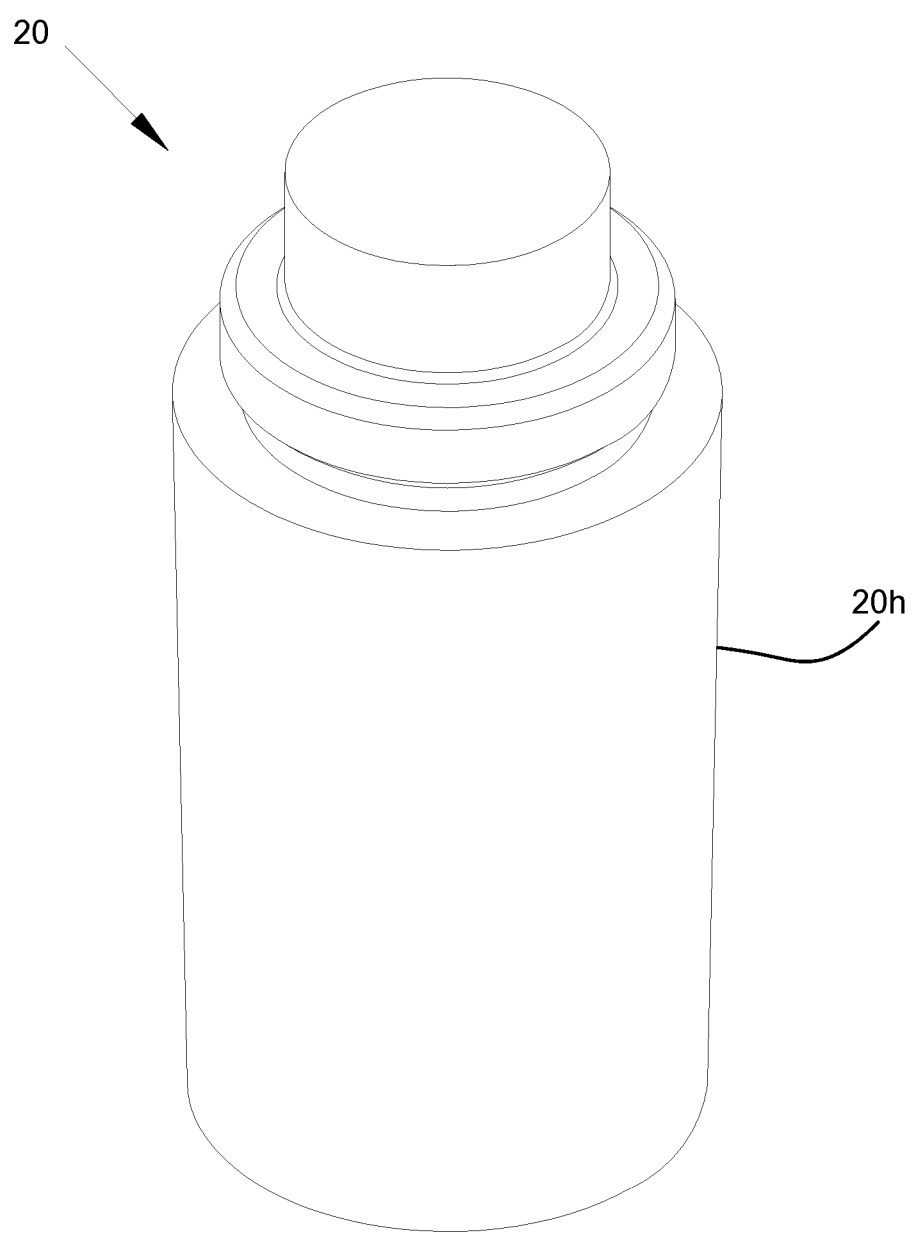
FIG. 1 is an isometric view of a device for removing beam energy according to one embodiment of the present invention.

Embodiments of the present invention can include a device for removing energy from an electromagnetic radiation beam. The beam energy removal device can include, but is not limited to, a body being a solid mass of an energy/light transmissive material having a substantially similar refractive characteristic to a liquid to be assayed. For instance, the beam energy removal device can be a single block of material having one of a plurality of different shapes. For instance, the block of material can have a substantially cylindrical shape. Generally, the body can be coated in an energy absorbing material. For instance, an outside surface of the device can be coated in an energy absorbing material.

In one embodiment, the beam energy removal device can be implemented with a turbidity measuring device. The beam removal device can be located adjacent to a measurement chamber of the turbidity measuring device to which the beam removal device can be operatively coupled. Typically, the beam energy removal device can have a shape and geometric characteristics designed to facilitate a capture of energy of a beam and reduce a risk of errant energy being reflected back into the measurement chamber where a portion could be incident on a detector housed therein.

Typically, the beam energy removal device can be implemented to improve a minimum detection limit of a liquid assay by preserving an integrity of energy absorbing surfaces submersed in a liquid used to absorb energy of an interrogating beam subsequent to assay. Energy absorbing surfaces submerged in a liquid can degrade from corrosion, chemical reaction, photo-bleaching and bubbles which can interfere with the assay process by scattering beam energy as result of changes in the characteristics of energy absorptive surfaces. Changes in the characteristics of energy absorbing surfaces whereupon an interrogating beam is incident can mimic traits exhibited by the liquid (e.g., absorbance, scatter, or photoluminescence) that can be deleterious to the assay process.

Typically, embodiments of the turbidity measuring device can include, but are not limited to, a fluidic module and a measurement module. The fluidic module can include a deaerator for removing entrained air and/or gases from a liquid sample. In one instance, the deaerator can be a combination of components or a sub-assembly of the fluidic module. When a liquid sample containing entrained gases is assayed, the gases can mimic the optical phenomenon of absorption, scatter, or fluorescence upon interrogation of the liquid sample by a beam of light, which can be deleterious to the assay process. The fluidic module can include the deaerator to minimize and/or remove entrained gasses in a liquid sample prior to the liquid sample being interrogated by the measurement module. The turbidity measuring device can be implemented as, but is not limited to, a turbidimeter, a fluorometer, and a nephelometer.

As previously mentioned, because embodiments of the beam energy removal device are configured to be removably coupled to the measuring instrument, an actual variation of the device including the material from which the device is made, the type of energy absorbing coating/material used, and the geometric configuration of the device can be chosen based on the type of liquid being assayed and the specific wavelengths of the light beam being used as part of the assay. As can be appreciated, this permits a particular measurement instrument to be potentially used with a greater number of analyte fluids and with light beams of differing wavelengths while still maintaining a high degree of effectiveness and minimum introduction of error due to errant light/energy.

Embodiments of the present invention can offer one or more of the following advantages over prior art energy/light traps. Because the beam energy removal device is not located in a measurement chamber, the energy removal device does not alter a flow of a liquid analyte, thereby permitting faster response times and quicker analyte turnover. A volume of the measurement chamber of an associated analytical instrument can be reduced allowing faster response times compared to prior art instruments wherein the energy trap is built into the chamber. As can be appreciated, a risk of heating the surfaces of the energy trap and causing a liquid in contact therewith to outgas and form bubbles on surfaces of the energy trap surfaces can be eliminated. As a result, an integrity of the measurement made by the associated instrument can be improved. Light absorbing materials of the energy removal device can never come into contact with the liquid analyte. Materials can be chosen for maximum effectiveness without concern over degradation in certain environments. Finally, the energy removal device can be configured to be easily replaceable allowing a particular variation of the device to be chosen to fit the nature of the analysis being performed and the type of liquid on which the analysis is being performed. For instance, a particular variation of the device can be chosen to be made of materials matching a refractive index and other optical properties of the liquid analyte.

In one embodiment, the beam dump can include a substrate material that can be low in thermal conduction to insulate absorbed energy from a liquid sample through which a beam of energy is transmitted. The substrate material can further be (i) transparent to a wavelength(s) comprising the beam of energy to be absorbed, (ii) chemically compatible with a liquid sample, and (iii) possessing an index of refraction that is in close agreement to the index of refraction of the liquid sample under assay. As can be appreciated, the material comprising the beam dump can be selected for a first set of characteristics independent of energy absorbing material characteristics from a second set of characteristics. An arrangement of the energy absorbing surfaces within the monolithic substrate material of the beam dump hereinafter described can increase an overall energy removal of the beam dump.

One embodiment of the present invention can include a first method or process for removing energy from a beam. The first process can include, but is not limited to, ingress of energy through an optical surface into a beam dump comprised of a media transparent to the wavelengths of the energy beam, energy being impingent upon energy absorbing surfaces, energy being absorbed upon a first energy absorbing surface, residual energy being directed towards a second energy absorbing surface, residual energy being absorbed upon the second energy absorbing surface, residual energy being directed towards the first or the second energy absorbing surfaces, residual energy being absorbed upon the first or the second energy absorbing surfaces, and residual energy being discouraged from exiting the beam dump through the optical surface.

One embodiment of the present invention can include a second method or process for removing energy from a beam. The second process can include, but is not limited to, ingress of energy through an optical surface into a beam dump comprised of a media transparent to the wavelengths of the energy beam, energy being impingent upon energy absorbing surfaces, energy being absorbed and/or transmuted to a lower energy state upon a first energy absorbing surface, residual energy being directed towards a second energy absorbing surface, residual energy being absorbed and or transmuted to a lower energy state upon the second energy absorbing surface, residual energy being directed towards the first or the second energy absorbing surfaces, residual energy being absorbed or transmuted to a lower energy state upon the first or the second energy absorbing surfaces, and residual energy being discouraged from exiting the beam dump through the optical surface. The second process can reduce an energy of the beam by beam energy being absorbed by the first and the second energy absorbing surfaces and a reflection of any transmuted energy incident upon the optical surface.

One embodiment of the device for removing energy from a beam can include, but is not limited to, a body, an optical surface, a central axis, a first energy absorbing surface, a second energy absorbing surface, and an energy absorbing material disposed on the first and the second energy absorbing surfaces. The body can be comprised of a material that can be transparent to a beam of energy. Typically, the body can be defined by the optical surface, the central axis, the first energy absorbing surface, and the second energy absorbing surface. The optical surface can be adapted to make contact with a liquid in a turbidity measuring device the body is operatively coupled to. The central axis can be adapted to facilitate a beam of energy to propagate from the turbidity measuring device into the energy removal device substantially perpendicular to the optical surface. The first energy absorbing surface can be displaced longitudinally from the optical surface. The first energy absorbing surface can be comprised of three or more triangular facets with coincident sides to form a vertex coincident upon the central axis at a distance shorter than the base of the triangular facets. The second energy absorbing surface can be of revolution displaced radially about the central axis.

One embodiment of the present invention can include a device for removing energy from a beam. The energy removal device can include a body defined by an optical surface, a central axis, a first energy absorbing surface, a second energy absorbing surface, and an energy absorbing material disposed upon the first and the second energy absorbing surfaces. The body can be comprised of a media transparent to the beam of energy. The optical surface can be adapted to make contact with a liquid in a turbidity measuring device. The central axis can be adapted to facilitate the beam of energy to propagate from the turbidity measuring device into the energy removal device substantially perpendicular to the optical surface. The first energy absorbing surface can be of revolution and displaced longitudinally from the optical surface and radially symmetric about the central axis. The second energy absorbing surface can be of revolution displaced radially about the central axis of a larger radii than the first energy absorbing surface of revolution.

One embodiment of the present invention can include a device for removing energy from a beam. The energy removal device can include a body defined by an optical surface, a central axis, a first energy absorbing surface, at least one second energy absorbing surface, and an energy absorbing material disposed upon the first and the second energy absorbing surfaces. The body can be comprised of a media transparent to the beam of energy. The optical surface can be adapted to make contact with a liquid in a turbidity measuring device. The central axis can be adapted to facilitate the beam of energy to propagate from the turbidity measuring device into the energy removal device substantially perpendicular to the optical surface. The first energy absorbing surface can be inclined at an oblique angle to the central axis and can be displaced longitudinally from the optical surface. The at least one second energy absorbing surface being displaced from the central axis substantially parallel to the central axis, where the first and the at least one second energy absorbing surfaces terminate to form a wedge.

One embodiment of the present invention can include a device for removing energy from a beam. The energy removal device can include a body defined by an optical surface, a central axis, a first polyhedron energy absorbing surface, a second energy absorbing surface of revolution, and an energy absorbing material disposed upon the first and the second energy absorbing surfaces. The body can be comprised of a media transparent to the beam of energy. The optical surface can be adapted to make contact with a liquid in a turbidity measuring device. The central axis can be adapted to facilitate the beam of energy to propagate from the turbidity measuring device into the energy removal device substantially perpendicular to the optical surface. The first energy absorbing polyhedron surface can be displaced longitudinally from the optical surface and can be comprised of three or more pairs of triangular facets with one coincident side to form an edge. The edges can be convergent upon the central axis at a distance longer than the vertex of the triangular facets and one other side of each triangular facet can be coincident with the second energy absorbing surface of revolution radially displaced about said central axis.

Embodiments of the present invention can be utilized with a deaerator apparatus for liquid assay as is described in U.S. provisional patent application 62/173,101, filed on Jun. 9, 2015, titled "DEAERATOR APPARATUS FOR LIQUID ASSAY", and having the same inventor as the present application, and is herein incorporated by reference in its entirety.

The following PCT applications are incorporated by reference in their entirety: PCT/US16/35638, filed Jun. 3, 2016, titled "TURBIDITY MEASURING DEVICE; and PCT/US16/36202, filed Jun. 7, 2016, titled "BACKSCATTER REDUCTANT ANAMORPHIC BEAM SAMPLER".

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, vertical, horizontal, back, front and lateral are relative to each other and are dependent on the specific orientation of a applicable element or article, and are used accordingly to aid in the description of the various embodiments and are not necessarily intended to be construed as limiting.

The term "light," as used in the specification and appended claims, refers to electromagnetic radiation in the visible spectrum.

A First Embodiment of a Device for Removing Energy from a Beam

Referring to FIG. 1, a detailed diagram of a first embodiment 20 of a device is illustrated. The device 20 can be implemented to remove and/or absorb a light beam or other beam of electromagnetic radiation. For instance, the beam dump 20 can be used to absorb a beam of light from a liquid being assayed in a turbidity measuring device.

The beam dump 20 shown in FIG. 1 can be configured to absorb energy from a beam of light and dissipate the absorbed energy as heat without transference of said heat to a liquid sample. In one embodiment, the beam dump 20 can be of monolithic construction transparent to a spectral content of an energy beam and of a material that can be low in thermal conduction. For example, the material can have a thermal conduction of less than 3 W/(m·° K). Material classes possessing suitable chemical resistance and optical and thermal properties can include, but are not limited to, plastics, polymers, glass, silica, and ceramics.

Figure 2:
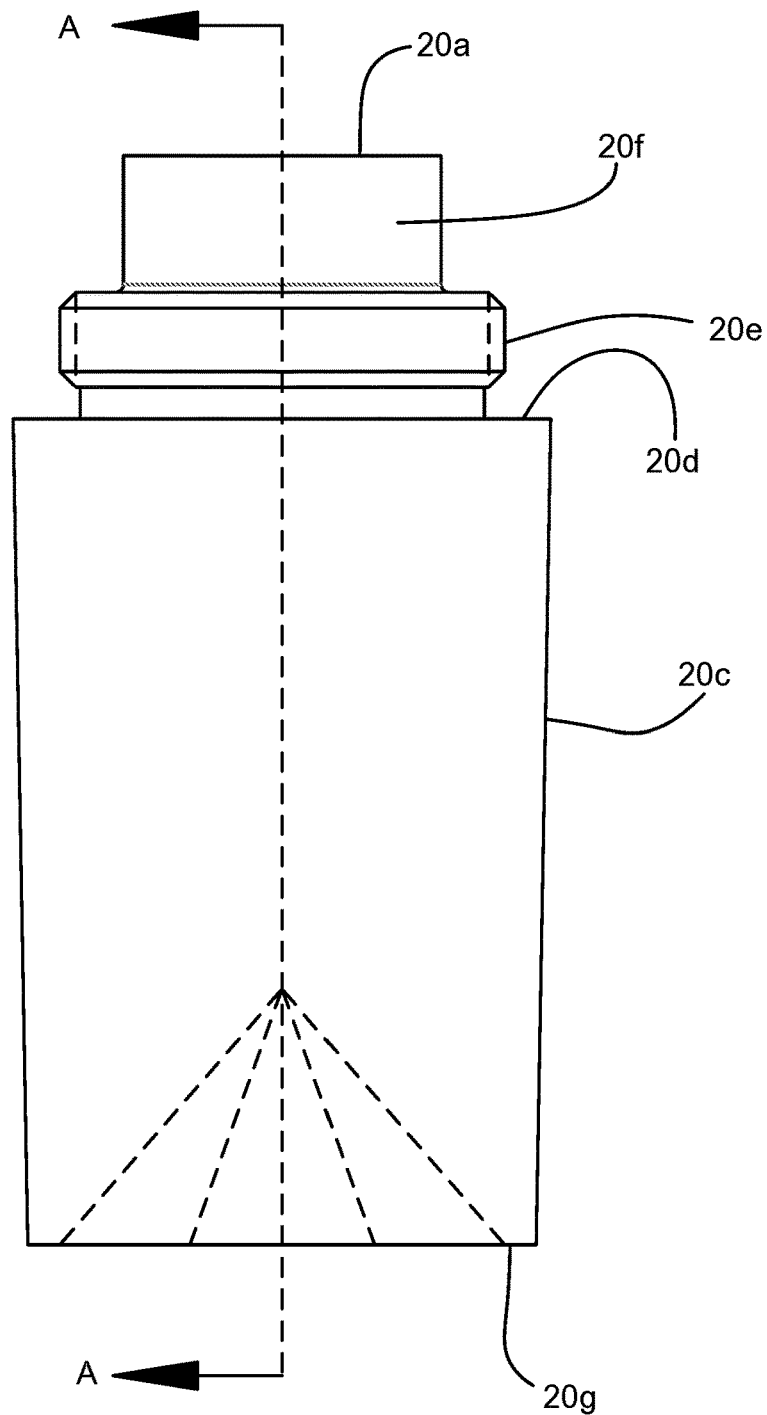
FIG. 2 is a side view of a device for removing beam energy with cross-section assignment A-A according to one embodiment of the present invention.
Figure 3:
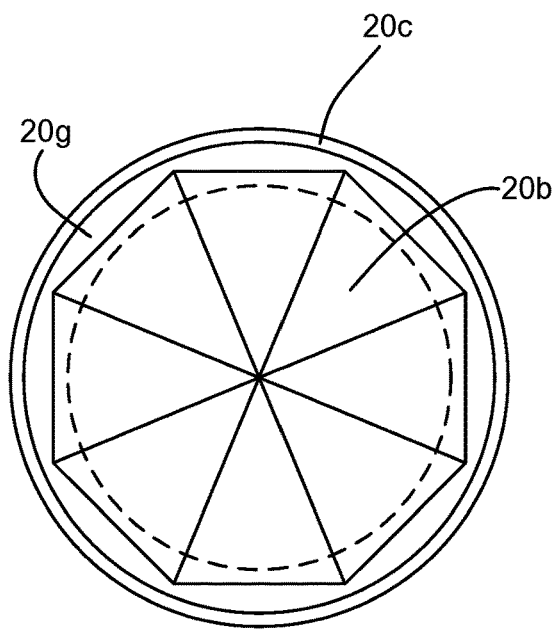
FIG. 3 is a bottom view of a device for removing beam energy according to one embodiment of the present invention.
Figure 4:
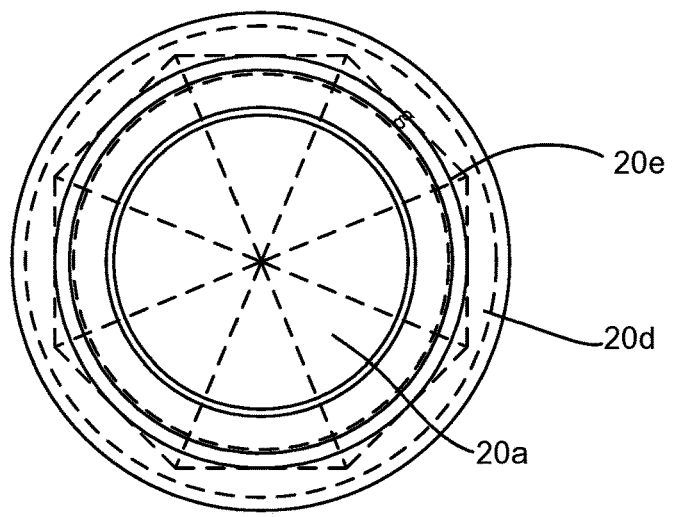
FIG. 4 is a top view of a device for removing beam energy according to one embodiment of the present invention.

Referring to FIGS. 2-4, a side view, a bottom view, and a top view, respectfully, of the beam dump 20 are illustrated.

The beam dump 20 can include, but is not limited to, a solid block (or body) 20h, an optical surface 20a, a first energy absorbing surface 20b, a second energy absorbing surface 20c, a seating surface 20d, a threaded feature 20e, a cylinder feature 20f, and a terminate surface 20g. As shown, the solid block 20h can have a substantially cylindrical shape and can be comprised of a material that will hereinafter be referred to as the substrate material.

The optical surface 20a can be placed in direct contact with a liquid in a turbidity measuring device (described hereinafter) being assayed for an ingress of beam energy into the beam dump 20. The first energy absorbing surface 20b can be a surface comprised of polygon facets. For example, the polygon facets are depicted as an 8-sided polygon, forming a substantially pyramidal shape. As can be appreciated, the first energy absorbing surface may form a polygon of any number of facets of three or greater. Typically, the first energy absorbing surface 20b can include an apex. The second energy absorbing surface 20c can be a surface having a substantially cylindrical shape. The seating surface 20d and the threaded feature 20e can be implemented to couple the beam dump device 20 to the turbidity measuring device. The seating surface 20d, the threaded feature 20e, and the cylinder feature 20f can be used to attach, locate, and make a liquid tight connection between the beam dump 20 and a vessel of the measuring instrument containing the liquid sample or analyte.

The surfaces 20b, 20c, and 20g can be coated with an energy absorbing material judicially selected from materials exhibiting low reflectivity to wavelengths comprising a light beam to be absorbed. For instance, a reflectivity less than approximately 5% of an incident radiation can be implemented. The coating material can be selected from a class of materials including, but not limited to, paints, elastomers, and plastics. As can be appreciated, a material capable of good adhesion to the substrate material of the beam dump 20 can be selected.

Figure 5:
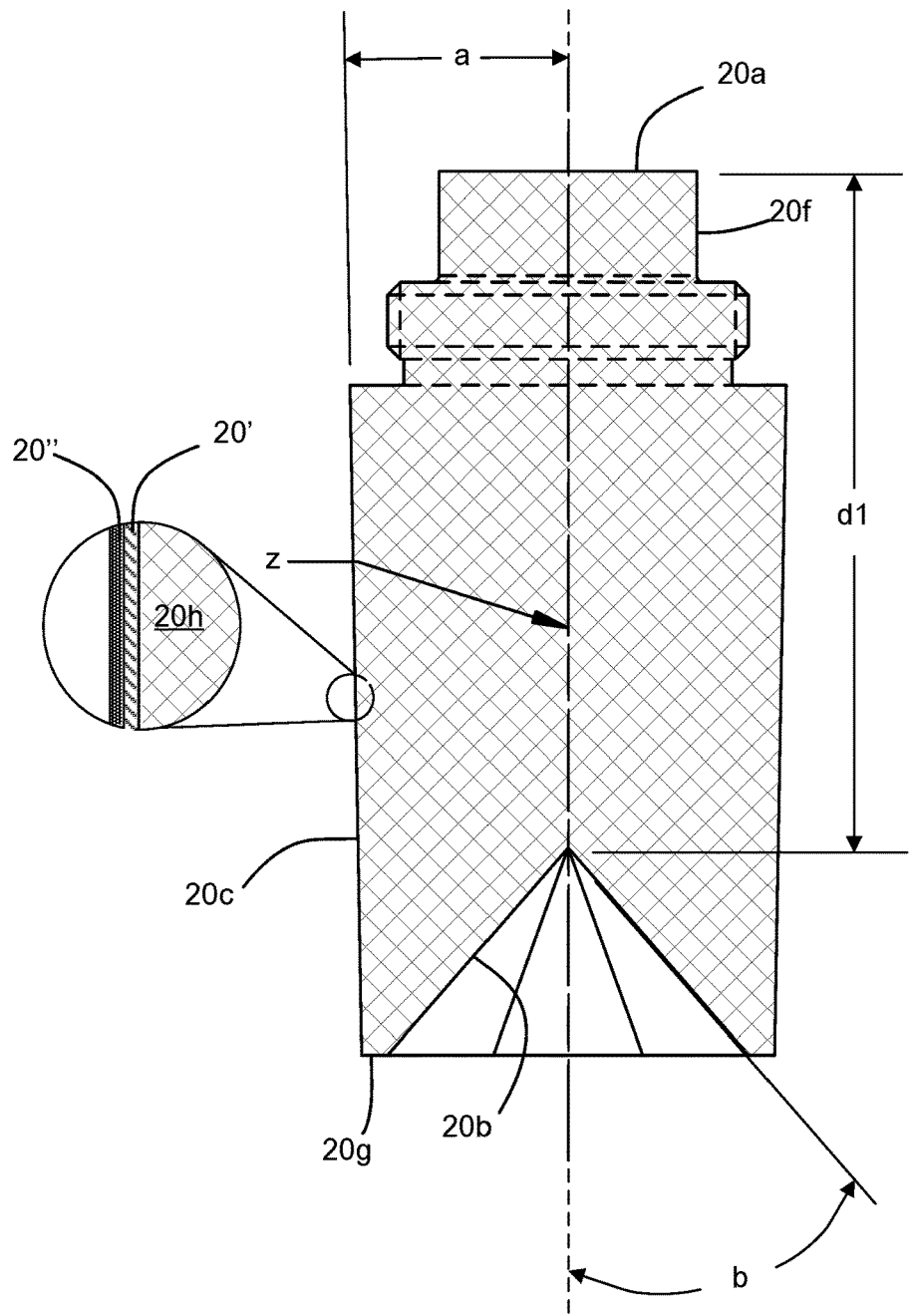
FIG. 5 is section view A-A of FIG. 2 of a device for removing beam energy according to one embodiment of the present invention.

As depicted in FIG. 5, the second energy absorbing surface 20c is shown with an energy absorbing coating 20' and an opaque coating 20". As can be appreciated, each of the energy absorbing surfaces can include the energy absorbing coating 20' and the opaque coating 20". The light absorbing coating 20' can be in intimate contact with the substrate material 20h of the beam dump 20, so as low a refractive difference can exist between the substrate material 20h and the light absorbing coating 20'. The coating applied to the surfaces 20b, 20c and 20g can be opaque to prevent external radiation from entering the beam dump 20 by a way other than as intended through the optical surface 20a. The opaque coating 20" can be applied secondarily over the energy absorbing coating 20' to prevent external radiation from entering the beam dump 20 by a way other then as intended through the optical surface 20a. For instance, the opaque coating 20" can be implemented when a material selected to be the energy absorbing coating 20' is not sufficiently opaque to block external radiation from entering the beam dump 20. As can be appreciated, coatings that provide both energy absorbing properties and radiation blocking properties can be implemented, as mentioned hereinafter. As shown, the polygon facet 20b is depicted as part of a plurality of facets that form an octagonal pyramid; however, pyramids of different types having 3 or more polygonal facets may be implemented.

One example of the energy absorbing coating 20', which is also opaque, is KRYLON® 'Black Satin' acrylic paint no. 51613. Another example of the energy absorbing coating 20' is RUST-OLEUM® 'Gloss Black' epoxy paint no. 7886.

One example of an energy absorbing coating 20' that is not opaque is an interference coating. As is well known in the art, these types of coatings are usually proprietary to optical manufacturers of such coatings which are typically applied by vapor deposition process. An interference coating would need the additional opaque coating 20" previously described.

In one embodiment, the substrate material 20h of the beam dump device 20 can have a refractive index in close match with the refractive index of the liquid sample to be tested to provide a high coupling efficiency of the energy beam as the beam propagates from the liquid sample into the beam dump 20 through the optical surface 20a. It is easily realized by those skilled in the art that various anti-reflective coatings may be applied to the optical surface 20a to improve the coupling efficiency of the energy beam to the beam dump 20.

As an example, a liquid with a low refractive index, for instance water with a refractive index of 1.33, can be matched to a substrate material 20h of CYTOP® with a refractive index of 1.34. As another example, glycerol with a refractive index of 1.47, can be well matched to borosilicate glass with a refractive index of 1.47 or poly(methyl methacrylate) (PMMA) with a refractive index of 1.49. Of note, the refractive index match does not need to be an exact match. Wherein other constraints can be considered, for instance cost or material availability, tradeoffs may be made to select a substrate material that can limit the reflection loss of an acceptable value. For example, a reflection loss of less than 0.5% may be achieved by combining water with a substrate material of PMMA yielding a reflection loss of 0.33% at 589 nm.

As depicted in FIG. 5, the polygon facet(s) 20b can converge to an apex coincident with a centerline (z) at an incline angle (b). The second energy absorbing cylindrical surface 20c can be a cylindrical shape and may possess a taper angle (a) of a couple or few degrees to facilitate injection molding or is otherwise equal distance from the centerline (z) forming a right cylinder. The polygon facets 20b can be inclined at angle (b) so as the sum of angle (a) and (b) are less than 45 degrees. The optical surface 20a and the apex of the polygon facets can be spatially separated by a distance (d1).

Figure 6:
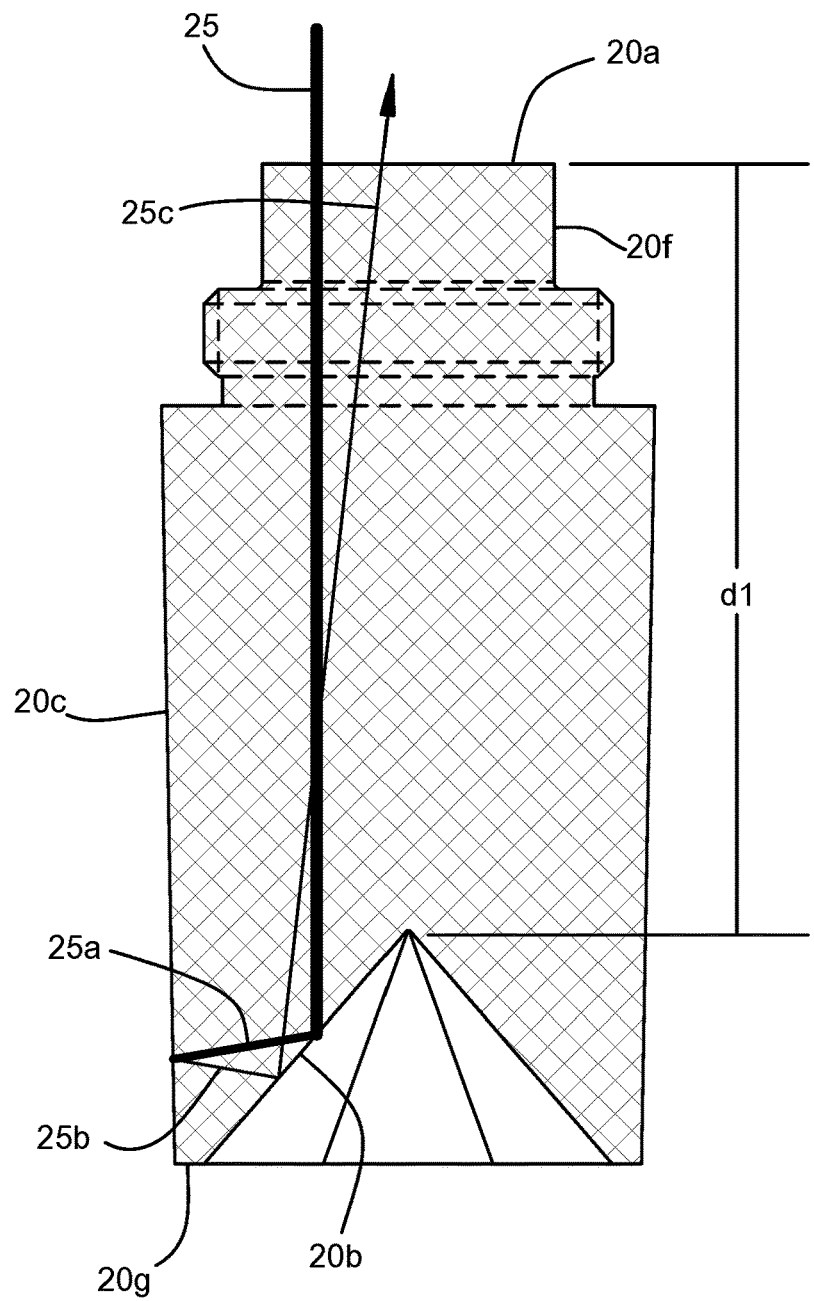
FIG. 6 is section view A-A of FIG. 2 of a device for removing beam energy according to one embodiment of the present invention depicting one ray path wherein energy is removed by the device.
Figure 7:
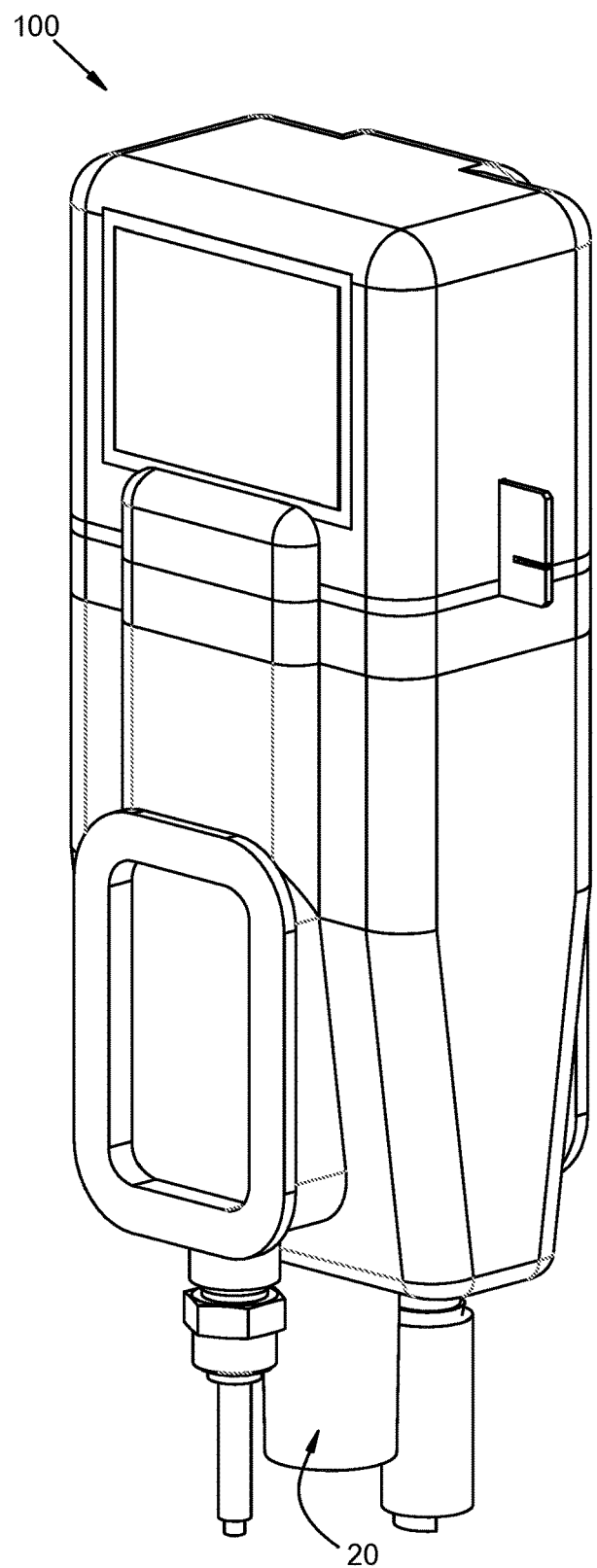
FIG. 7 is an isometric view of a turbidity measuring device for removing beam energy according to one embodiment of the present invention.

As depicted in FIG. 6, an energy beam ray 25 (e.g., beam of light) is shown as the energy beam ray 25 propagates through the beam dump 20. For illustrative purposes only, a line thickness is intended to represent pictorially an amount of energy in the ray 25, wherein a ray comprised of higher energy is illustrated by a thick line and at lower energy by a thinner line. The ray 25 can propagate through a liquid sample 21 (see FIG. 14) into the beam dump 20 by ingress through the optical surface 20a. The ray 25 can impinge on the first energy absorbing polygon surface 20b whereupon energy can be absorbed into the energy absorbing coating in contact with this surface. The residual portion of the ray 25a that is not absorbed can be directed towards the second energy absorbing cylindrical surface 20c, whereupon a significant portion of energy of the ray 25 can be absorbed into the energy absorbing coating in contact with the second absorbing cylindrical surface 20c. The residual portion of the ray 20c that is not absorbed can be directed back towards the first energy absorbing polygon surface(s) 20b, whereupon energy can be absorbed into the underlying energy absorbing coating.

For an energy absorbing material with a typical reflectivity of 2.1%, three incursions with the energy absorbing material can reduce the available energy to reenter the liquid sample along the ray path 25c to a value less than 1/100,000th of the original energy entering the beam dump.

Typically, the diameter of the cylinder forming the second absorbing cylindrical surface 20c can be larger than the diameter of the cylinder feature 20f, so as to obscure second energy absorbing cylindrical surface 20c from direct exposure to beam energy from above. Furthermore, the total surface area of first and second energy absorbing surfaces 20b, 20c can be substantially larger than a surface area of the optical surface 20a, thus reducing the probability that residual light will exit the beam dump 20 through the optical surface 20a.

Surfaces with low reflectance (e.g., energy absorbing surfaces) typically scatter light as a function of intensity that decreases as the cosine of the incident angle (i.e., such surfaces exhibit a predominately Lambertian reflectance characteristic). The second energy absorbing cylindrical surface 20c can be radiated indirectly from the first energy absorbing polygon surface(s) 20b at a distance greater than (d1) from the optical surface 20a. For the unique geometrical arrangement herein, the distance (d1), the diameter of cylinder feature 20f, and the diameter of the second energy absorbing cylindrical surface 20c can be selected so as to minimize the intensity and probability that energy scattered within the beam dump 20 will exit through the optical surface 20a. In one embodiment, the first energy absorbing polygon surface(s) 20b and the second energy absorbing cylindrical surface 20c can be inclined to an observer through the optical surface 20a at angles greater than approximately 30 degrees.

Other embodiments of the beam dump 20 are disclosed herein, which possess alternate geometries pertaining to the light absorbing surfaces. All the geometries can cause an energy beam entering the beam dump device to experience multiple incursions with light absorbing surfaces thereby absorbing more energy and making the value of the residual energy available to reenter the liquid sample satisfactorily small. The greater the number of incursions of the beam with the energy absorbing surfaces the higher the reflectivity of the energy absorbing material can be used to achieve similar beam energy removal results.

Wherein a beam of energy is comprised of wavelengths that readily cause excitation and reemission of energy at transmuted, lower energy state, (as an example, the phenomenon of fluorescence), the optical surface 20a may be modified to include an interference coating which transmits shorter wavelengths and rejects longer wavelengths. Furthermore, one or more of the energy absorbing surfaces may be modified to include an energy conversion constituent. Advantageously, a beam dump so modified can pass short wavelengths into the beam dump 20 through the optical surface 20a, wherein the energy can be absorbed and converted to longer wavelengths by one or more energy absorbing surfaces preventing short wave length energy, which the detector may be sensitive to, from exiting the beam dump 20 and reentering a measuring chamber of an associated instrument.

One embodiment of the energy beam dump 20 may be utilized in a turbidimeter (or nephelometer) to measure liquid samples having low levels of turbidity, typically less than 50 mNTU (Nephelometric Turbidity Units). A turbidimeter 100 is shown generally in FIGS. 7-15, incorporating the beam dump device 20. As will be described hereinafter, each of the disclosed beam dumps can be implemented with a turbidity measuring device.

Figure 8:
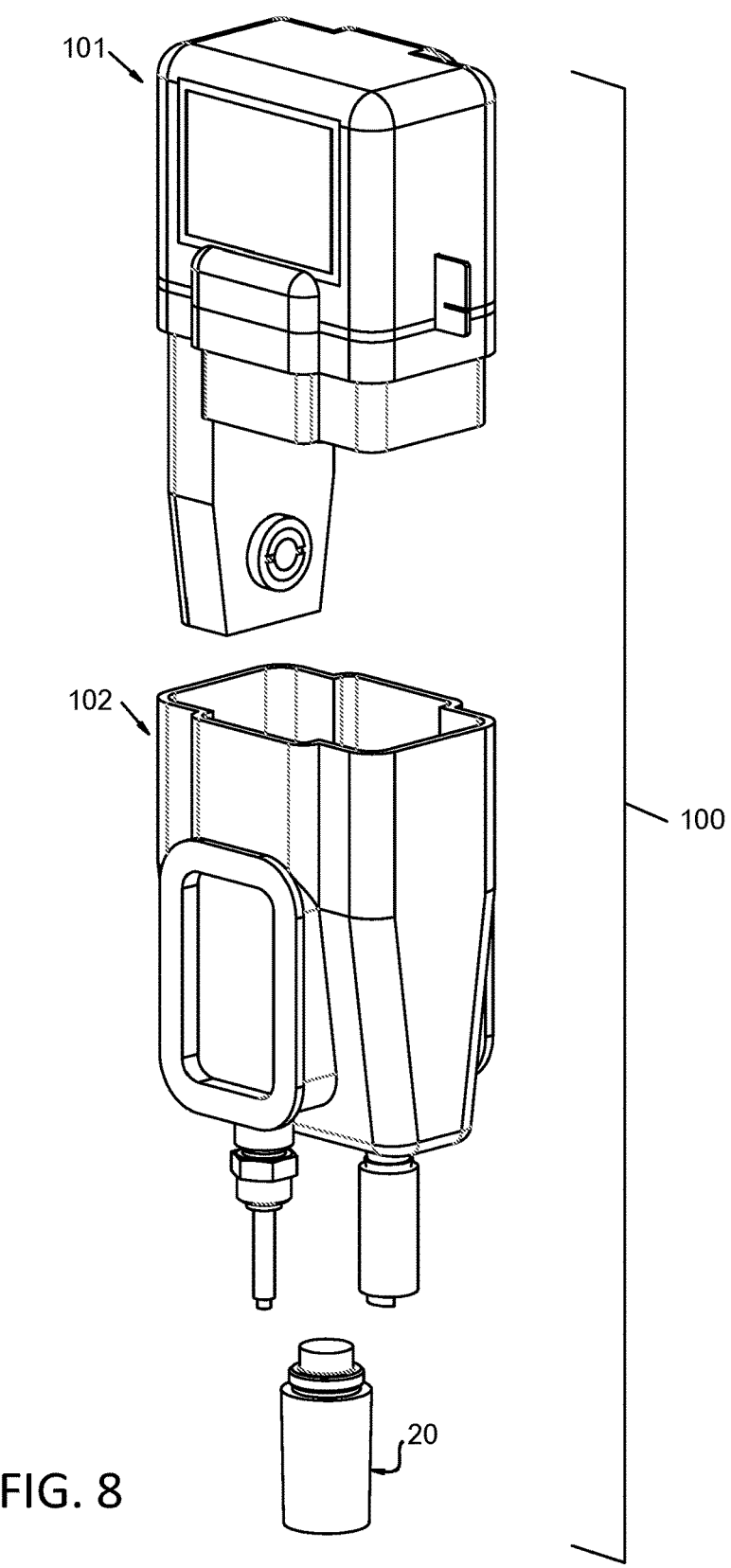
FIG. 8 is an exploded view of a turbidity measuring device for removing beam energy according to one embodiment of the present invention.

The turbidimeter 100, as shown in FIG. 8, can be comprised of three main components including, but not limited to, a measuring (or measurement) module 101, a fluidic module 102, and the beam dump 20.

As depicted in FIGS. 9-11, 13, and 15, front, bottom, top, side, and back views respectfully, the turbidimeter 100 can further include a flow vessel 1, an optic support 2, an optic cover 3, a display window 4, a display 5, an electrical connection 7a, an inlet front cover 14, an outlet cover 15, an inlet fitting 16, an inlet tubing 17, an ingress of a fluid sample 21a, an outlet fitting 18, an outlet tubing 19, the beam dump 20, and an egress of a fluid sample 21f.

Figure 9:
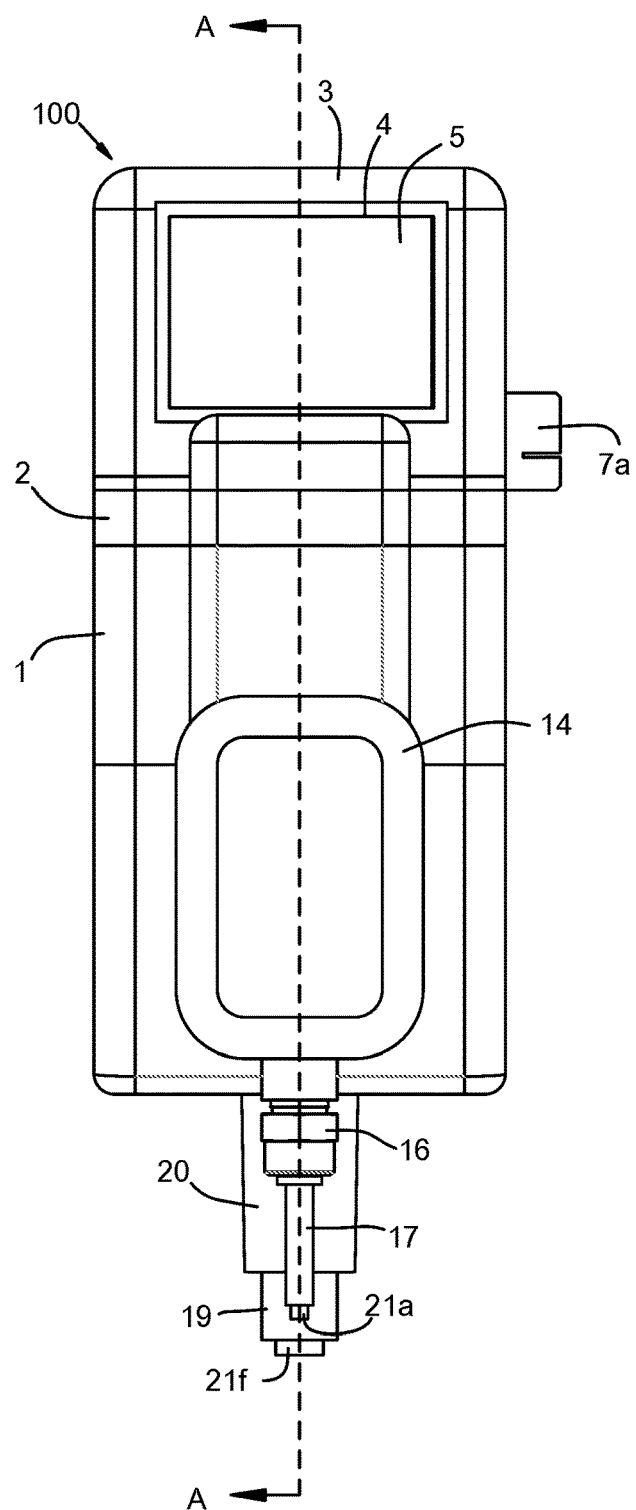
FIG. 9 is a front view of a turbidity measuring device for removing beam energy, with cross-section assignment A-A, according to one embodiment of the present invention.
Figure 10:
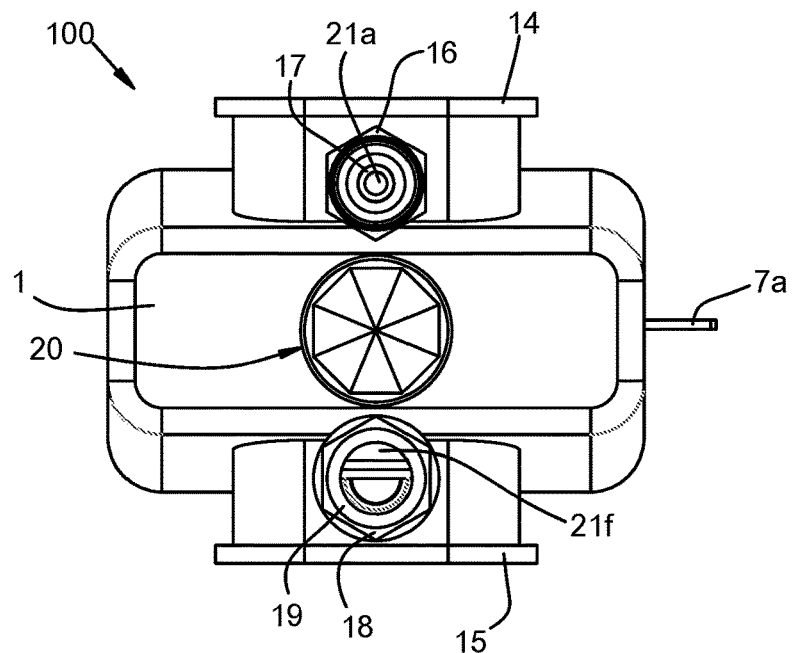
FIG. 10 is a bottom view of a turbidity measuring device for removing beam energy according to one embodiment of the present invention.
Figure 11:
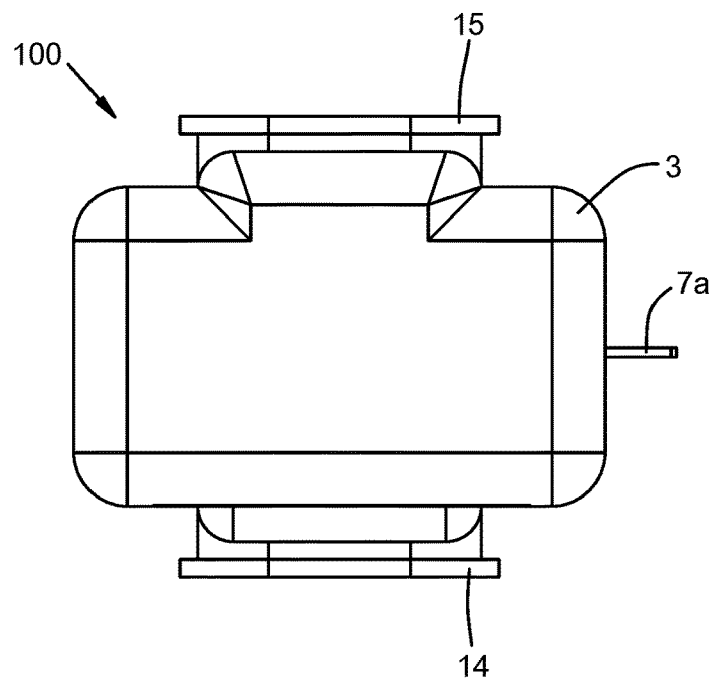
FIG. 11 is a top view of a turbidity measuring device for removing beam energy according to one embodiment of the present invention.
Figure 12:
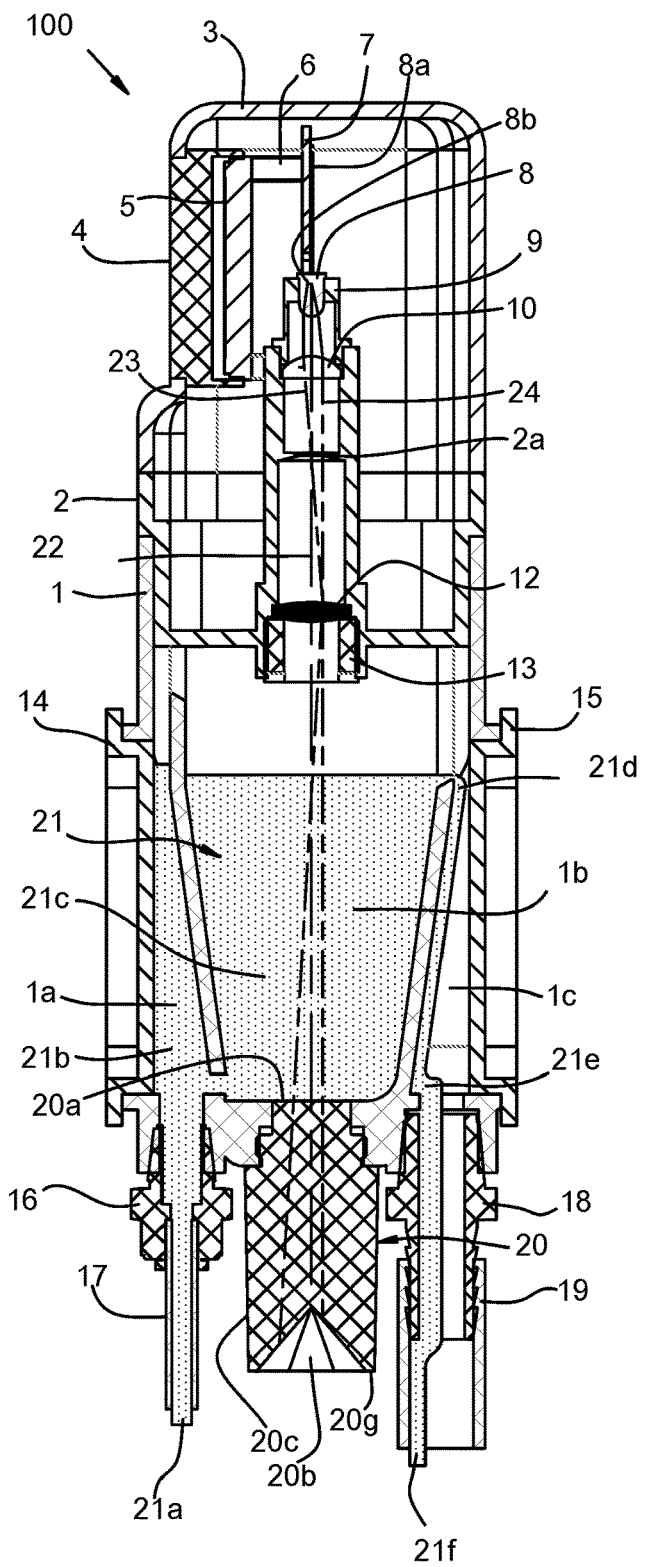
FIG. 12 is section view A-A, of FIG. 9, of a turbidity measuring device for removing beam energy according to one embodiment of the present invention.

As depicted in FIG. 12, section view A-A of FIG. 9 of turbidimeter 100, a liquid sample 21 can ingress into the flow vessel 1 through the inlet tubing 17 connected to the flow vessel 1 by the inlet fitting 16. The liquid sample 21 can flow into a deaerator chamber 1a formed between the front cover 14 and the flow vessel 1 and is identified as sample volume 21b. The liquid sample 21 can flow from the deaerator chamber 1a to the measurement chamber through a passage filling the measurement chamber with a sample volume 21c. The liquid sample 21 can spill over into an outlet chamber 1c formed between the outlet cover 15 and the flow vessel 1 over a weir in the flow vessel 1 and is identified as sample stream 21d. The liquid sample 21 can flow through the outlet chamber 1c, the outlet fitting 18, and the outlet tubing 19 and is identified as sample flow 21e. The liquid sample 21 can egress from the turbidimeter 100 through the outlet tubing 19 and is identified as sample flow 21f.

Energy from a light source 8 (e.g. an LED) can be formed into a beam by a plano-convex lens 10 and a bi-convex lens 12 along a centerline 22. Light can be emitted from an emitter 8b of the light source 8. The light source 8 can be provided power through electrical leads 8a and a printed circuit assembly 7. The light source 8 can be positioned relative to the plano-convex lens 10 through an optic mount 9 that can be press fit into an illuminator support 2. A chief light ray 23 can be emitted from the light source 8 and pass through the center of a light stop 2a. The light stop 2a can be positioned between the plano-convex lens 10 and the bi-convex lens 12 at one focal length from each lens within the optic support 2. The bi-convex lens 12 can be held in position by a retaining ring 13. A marginal ray 24 can pass through the light stop 2a parallel to a centerline 22 and can be refracted by the bi-convex lens 12 to form an image of the light stop 2a at one focal length from the bi-convex lens 12 within the liquid sample 21. The focal length of the bi-convex lens 12 can be selected so that the image of the light stop 2a can be in a forefront of the detector means, thus the illuminated field that may be in view of the detector means illuminates the liquid sample uniformly.

The focal length of the bi-convex lens 24, the distance from the light stop 2a, the diameter of light stop 2a, and the distance to the beam dump 20 can determine a size of the beam impingent upon the optical surface 20a of the beam dump 20. It is important that the diameter of the beam entering the beam dump 20 be smaller in diameter than the diameter of the optical surface 20a so that no beam energy may be dissipated within the sample volume 1b, which can interfere with the liquid assay. Judicious selection of the bi-convex lens 24 focal length, the diameter of the light stop 2a, the diameter of the optical surface 20a of the beam dump 20, and the relative spatial relation to one another must be carefully considered in order that the optical system of the turbidimeter 100 operates in accordance with the invention as described.

Figure 13:
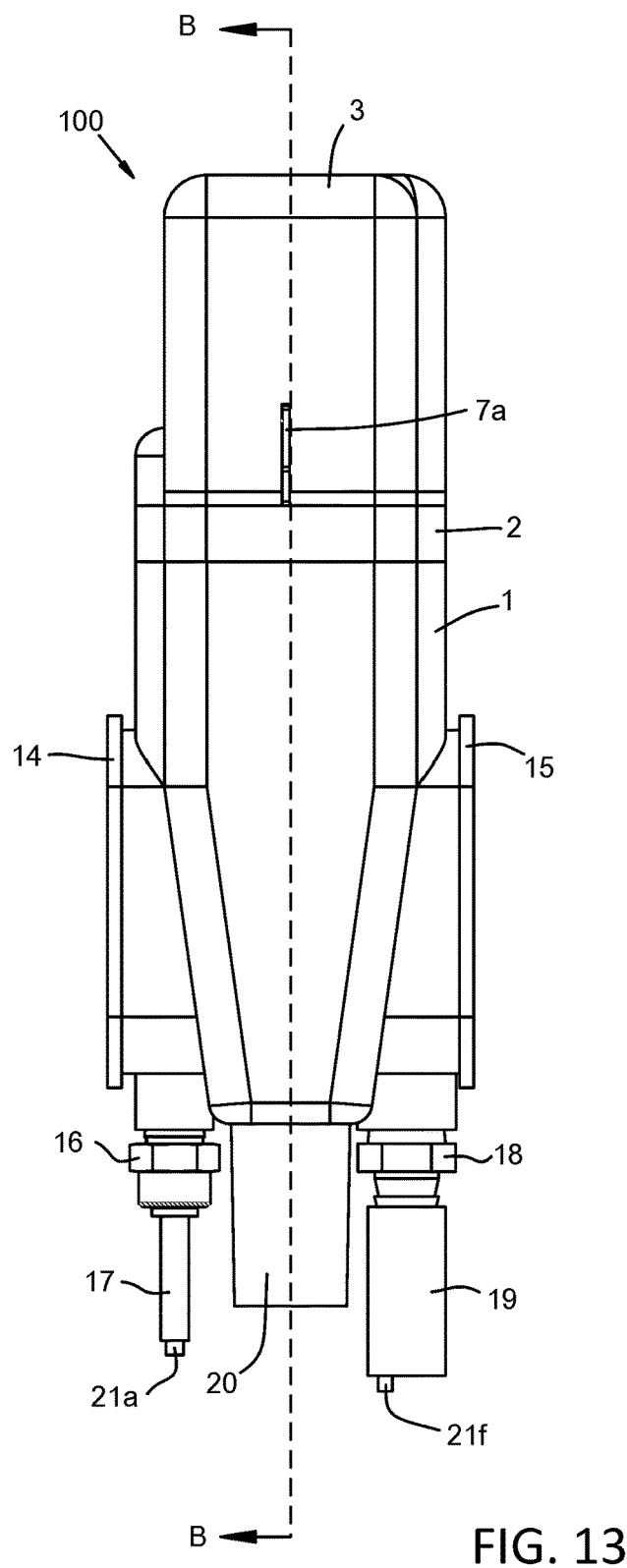
FIG. 13 is a side view of a turbidity measuring device for removing beam energy, with cross-section assignment B-B, according to one embodiment of the present invention.
Figure 14:
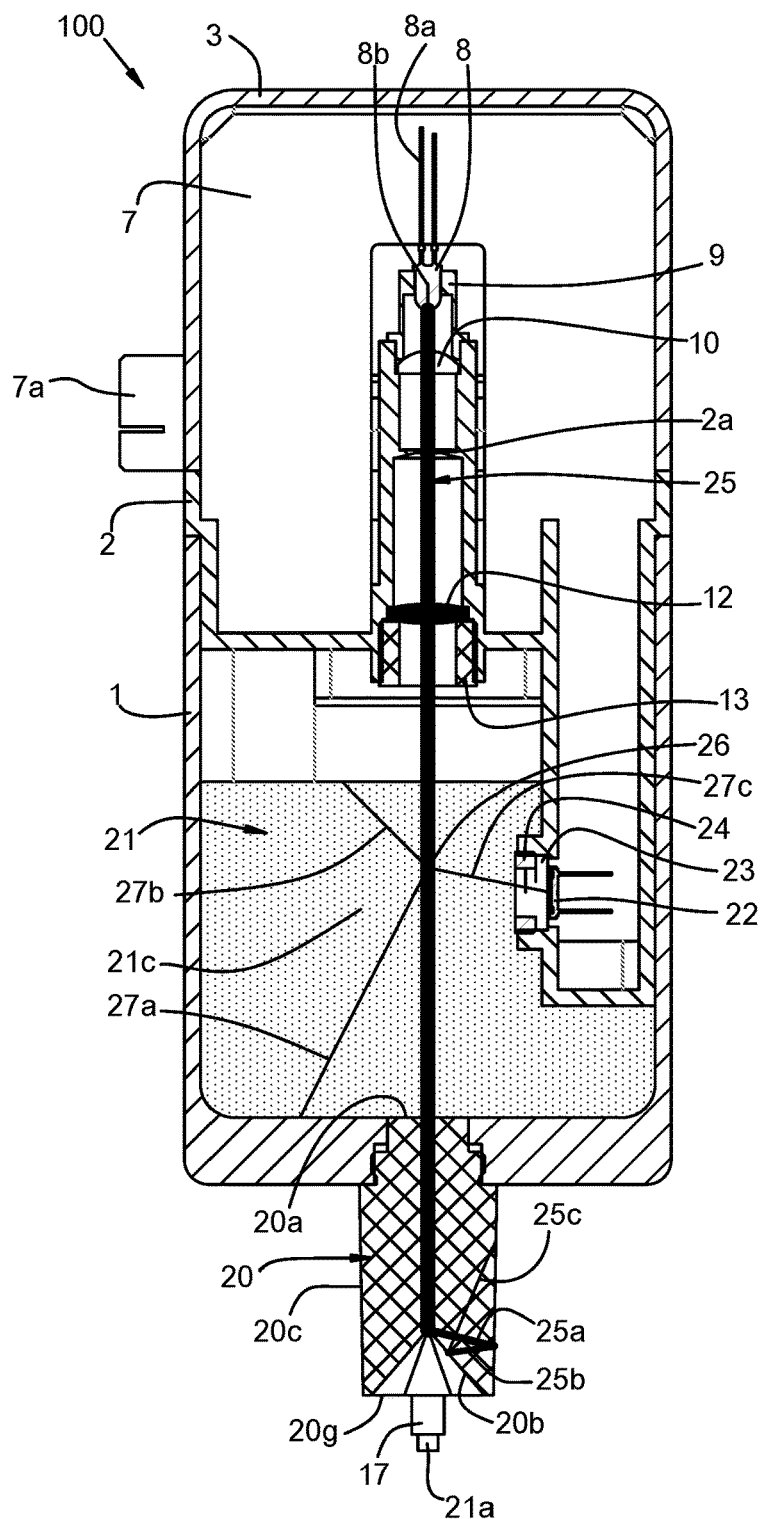
FIG. 14 is a section view B-B, of FIG. 13, of a turbidity measuring device for removing beam energy according to one embodiment of the present invention depicting one ray path wherein energy is removed by the invention.
Figure 15:
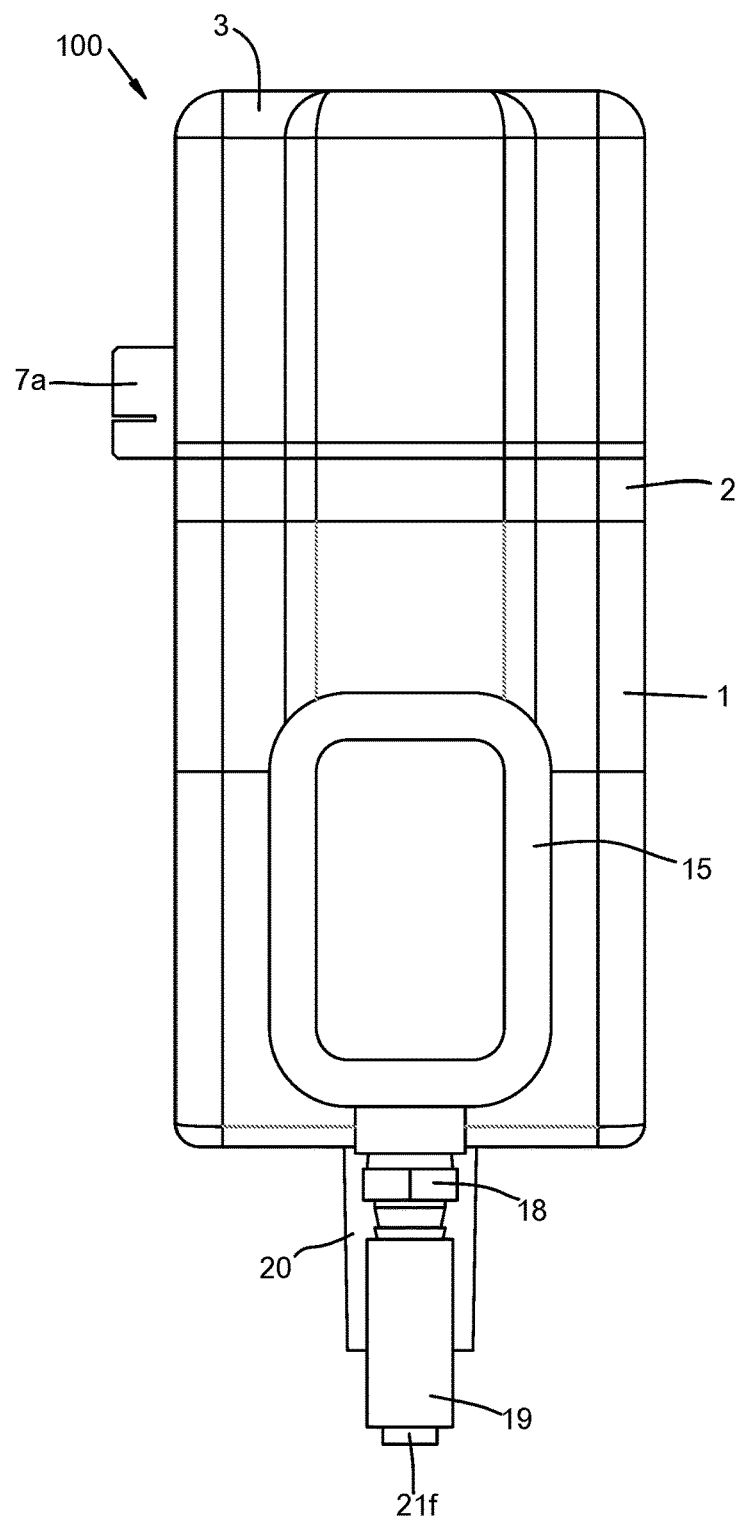
FIG. 15 is a back view of a turbidity measuring device for removing beam energy according to one embodiment of the present invention.
Figure 16:
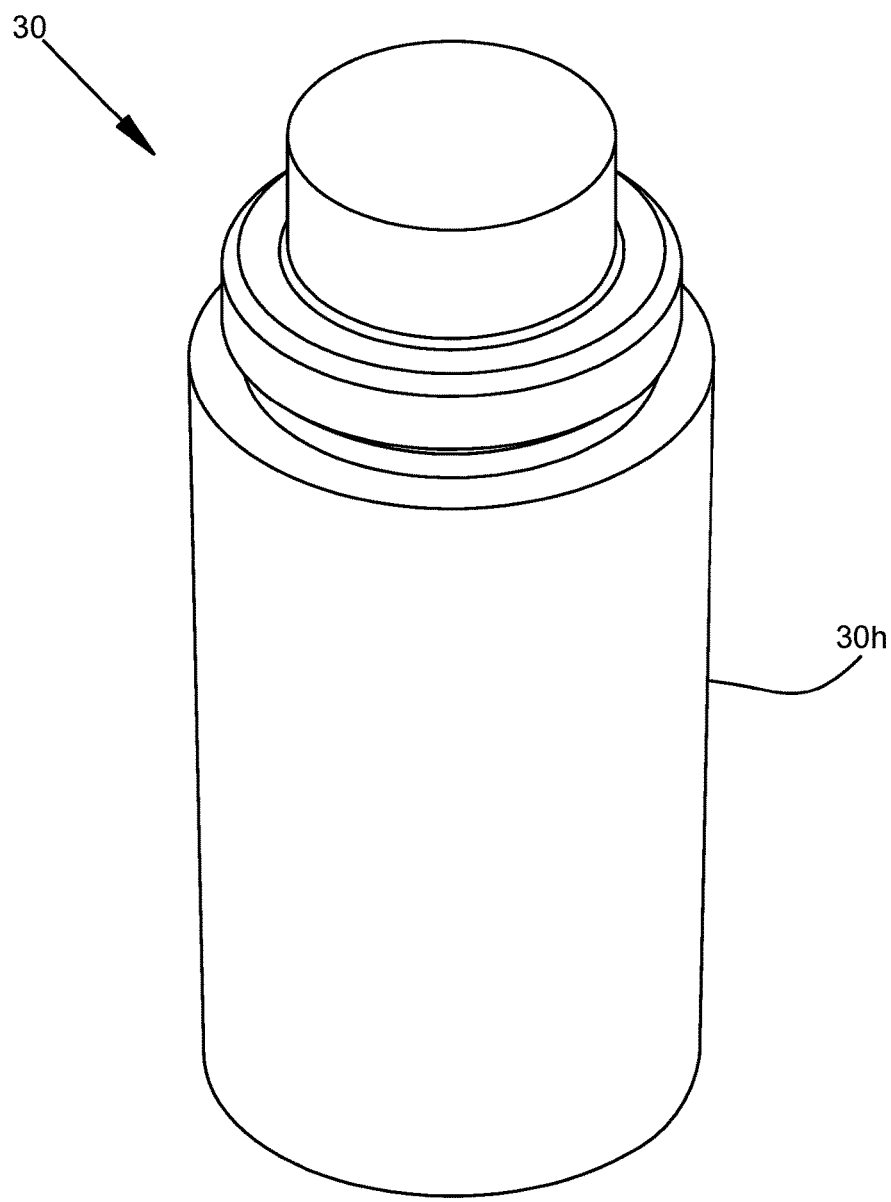
FIG. 16 is an isometric view of a device for removing beam energy according to a second embodiment of the present invention.
Figure 17:
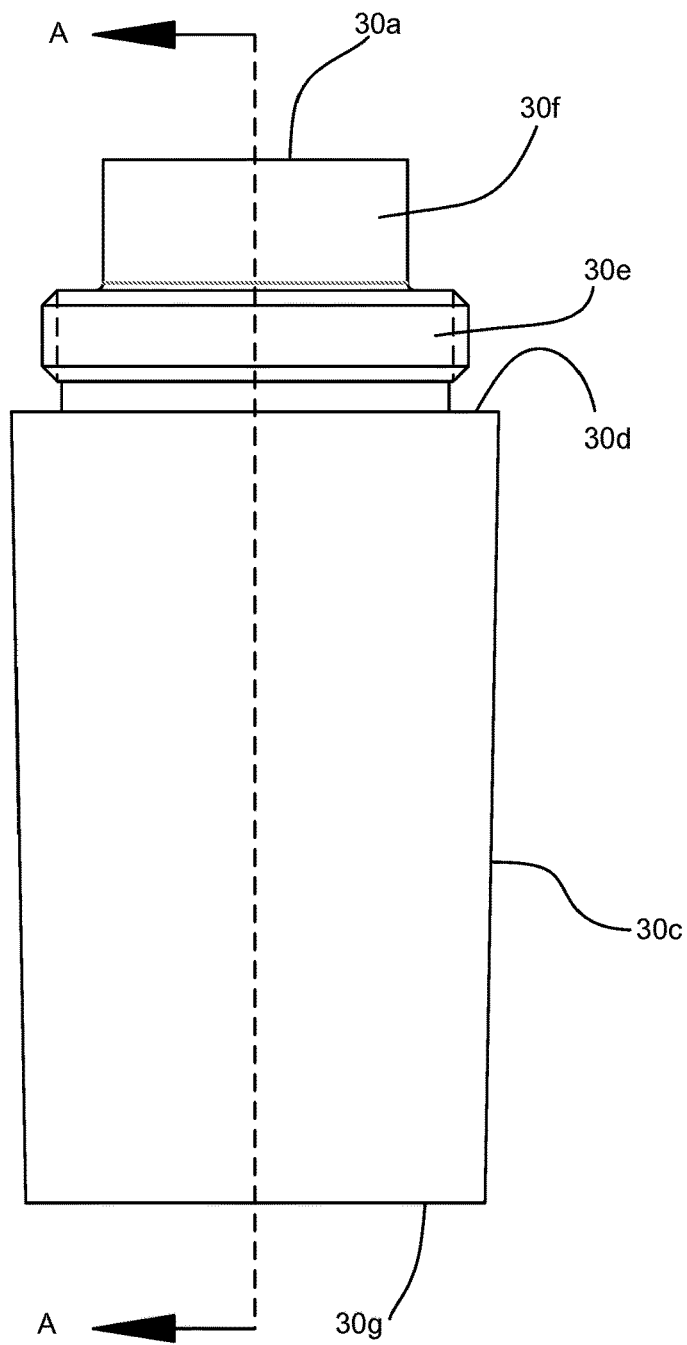
FIG. 17 is a side view of a device for removing beam energy, with cross-section assignment A-A, according to a second embodiment of the present invention.
Figure 18:
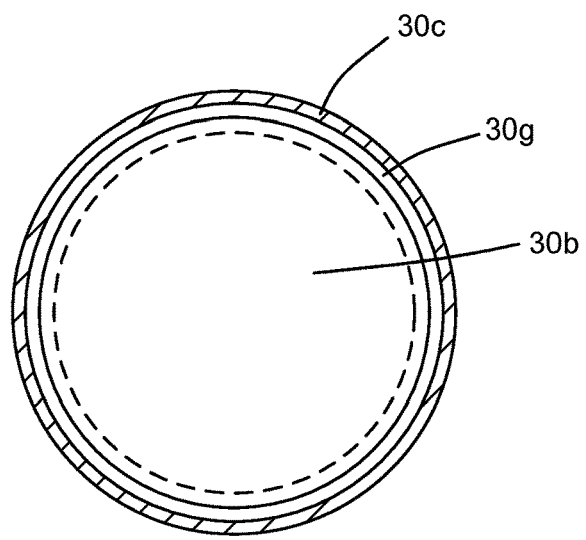
FIG. 18 is a bottom view of a device for removing beam energy according to a second embodiment of the present invention.
Figure 19:
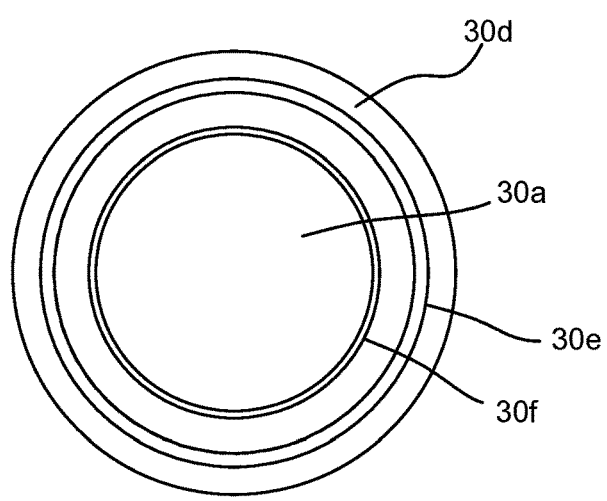
FIG. 19 is a top view of a device for removing beam energy according to a second embodiment of the present invention.

As depicted in FIG. 14, a section view B-B of FIG. 13, energy can be emitted from the emitter 8b of the light source 8 and formed into the energy beam 25 by means of the plano-convex lens 10, the light stop 2a, and the bi-convex lens 12 as described prior. The light beam 25 can be transmitted through the liquid sample 21 wherein a portion of the light can be scattered in possible directions as light rays 27a, 27b, and 27c within the sample volume 21c as a result of interaction of the light beam 25 and particles 26 in suspension of the liquid sample 21. The light ray 27c can be scattered in a direction so as to fall incident upon a detector 22 (e.g., a photodiode) through an optical element 23 held to the optic support 2 by a retaining ring 24. Through photo-electric effect, the detector 22 can convert light falling incident upon the detector 22 into an electrical signal. A relationship can be correlated as to the particulate content of the liquid sample 21 relative to a strength of the electrical signal.

A significant majority of the energy beam 25 that is not otherwise subjected to interaction with particles in suspension of the liquid sample 21 can propagate through the sample volume 21c unimpeded to the beam dump 20. The energy beam 25 can enter the beam dump 20 through the optical surface 20a propagating towards the first energy absorbing polygon surface 20b. Unabsorbed energy 25a of the energy beam 25 can be directed towards the second energy absorbing cylindrical surface 20c. An unabsorbed energy 25b of the unabsorbed energy 25a can be subsequently directed back towards the first energy absorbing polygon surface 20b. For each successive interaction between the energy from the energy beam 25 and the first energy absorbing polygon surface 20b or the second absorbing cylindrical surface 20c, the remaining unabsorbed energy can be significantly diminished. Advantageously, heat may not be generated at the optical surface 20a nor is heat of any measurable amount conducted through the substrate of the beam dump 20 from the energy absorbing surfaces 20b, 20c, 20g to the optical surface 20a in contact with the liquid sample 21. Accordingly, bubbles may not be generated on the optical surface 20a as result of heating that could otherwise interfere with the liquid assay in the manner previously described.

A Second Embodiment of a Device for Removing Energy from a Beam

As depicted in FIGS. 16-21, a second embodiment of a device 30 for removing a beam of energy from a liquid is illustrated. Similar to the first embodiment beam dump 20, the second embodiment beam dump 30 can be comprised of a solid block of material selectively coated with an energy absorbing material. Although not illustrated, the second embodiment beam dump 30 can be implemented with the previously discussed turbidimeter 100.

The beam dump 30 can include, but is not limited to, a solid block (or body) 30h, an optical surface 30a, a first energy absorbing surface of revolution 30b, a second energy absorbing surface of revolution 30c, a seating surface 30d, a threaded feature 30e, a cylinder feature 30f, and a terminate surface 30g. The solid block 30h can have a substantially cylindrical shape and can be comprised of a material that will be referred to hereinafter as the substrate material.

The optical surface 30a can be adapted to be placed in contact with a liquid in the turbidity measuring device 100 for an ingress of a beam energy into the beam dump 30. The seating surface 30d, the threaded feature 30e, and the cylinder feature 30f can be used to attach, locate, and make a liquid tight connection between the beam dump 30 and the turbidity measuring device 100 containing a liquid sample.

The surfaces 30b, 30c, and 30g can each be coated with an energy absorbing material judicially selected from materials exhibiting low reflectivity to wavelengths of which the energy/light beam may be comprised. The energy absorbing coating can be in intimate contact with the substrate material of the beam dump 30, so as low a refractive difference exists between the substrate material and the energy absorbing coating. The coating applied to the surfaces 30b, 30c, and 30g can be opaque to prevent external radiation from entering the beam dump 30 by a way other than intended through the optical surface 30a. In one embodiment, an opaque coating can be applied secondarily over the energy absorbing coating to prevent external radiation from entering the beam dump 30 by a way other than as intended through the optical surface 30a. Generally, except for the geometric differences between the second embodiment beam dump 30 and the first embodiment beam dump 20 as well as operational differences resulting from the geometric differences, they are similar in terms of construction and operation.

Figure 20:
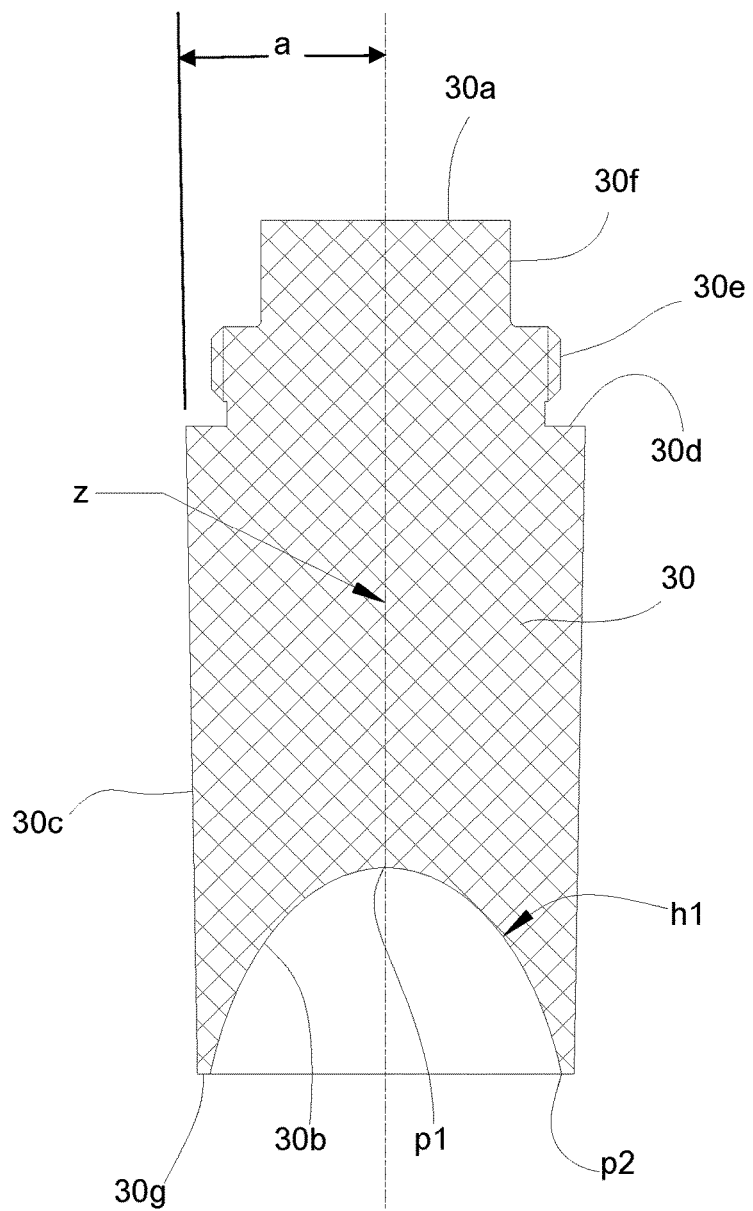
FIG. 20 is section view A-A, of FIG. 17, of a device for removing beam energy according to a second embodiment of the present invention.

As depicted in FIG. 20, the surface of revolution 30b is shown as a partial ellipse by example. It is to be appreciated that the surface of revolution 30b may be of any figure of line, smooth or erratic, connecting a first point (p1) located on central axis (z) to a second point (p2) located on terminate surface 30g. In one embodiment, the substrate material of the beam dump 30 may be selected from a material possessing a refractive index in close match to a refractive index of a liquid sample being assayed to ensure a high coupling efficiency as an energy beam propagates from the liquid sample into the beam dump 30 through the optical surface 30a. It is easily realized by those skilled in the art that various anti-reflective coatings may be applied to the optical surface 30a to improve the coupling efficiency of the energy beam to the beam dump 30.

Figure 21:
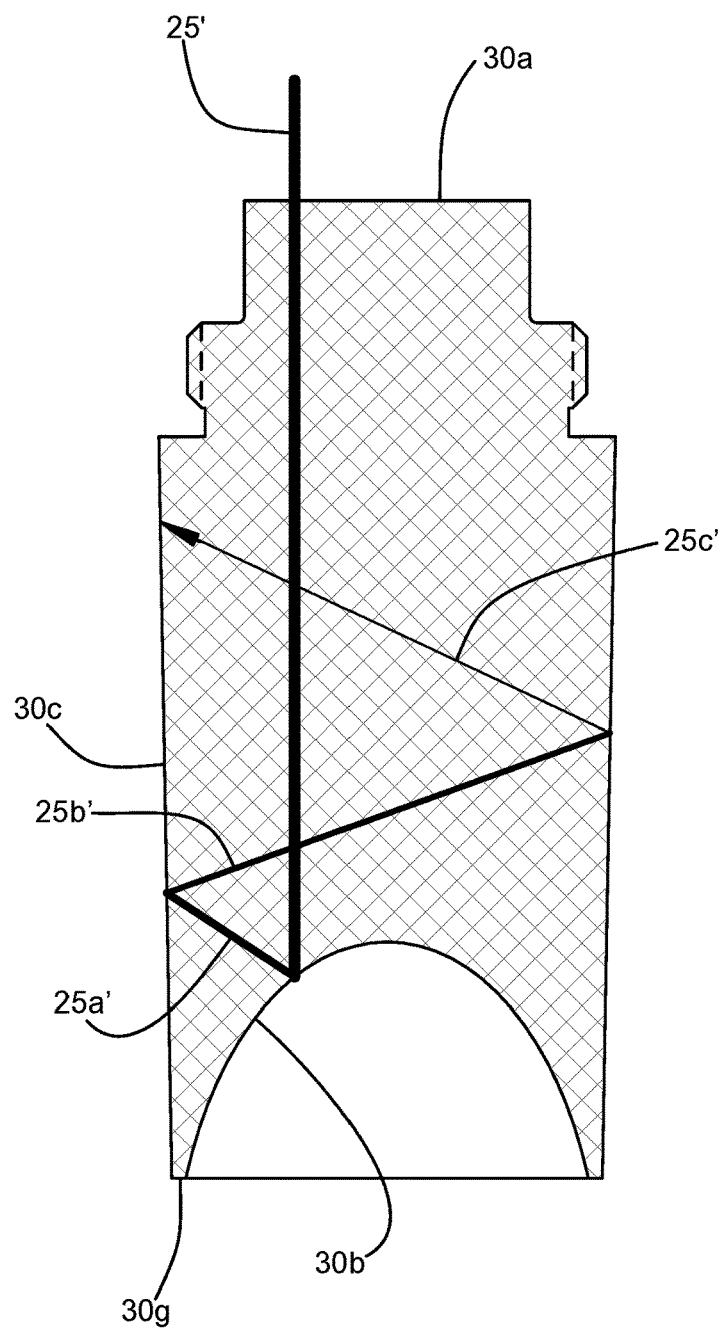
FIG. 21 is section view, A-A of FIG. 17, of a device for removing beam energy according to a second embodiment of the present invention depicting one ray path wherein energy is removed by the device.
Figure 22:
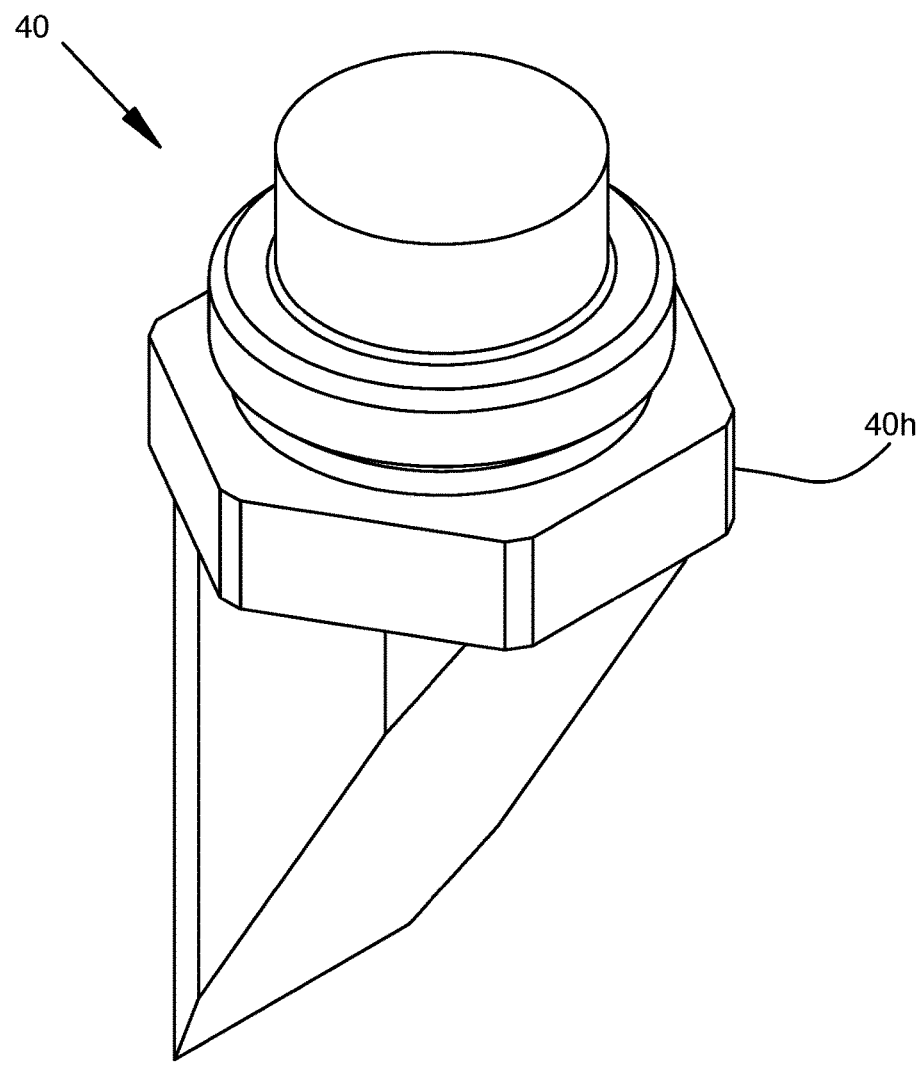
FIG. 22 is an isometric view of a device for removing beam energy according to third embodiment of the present invention.
Figure 23:
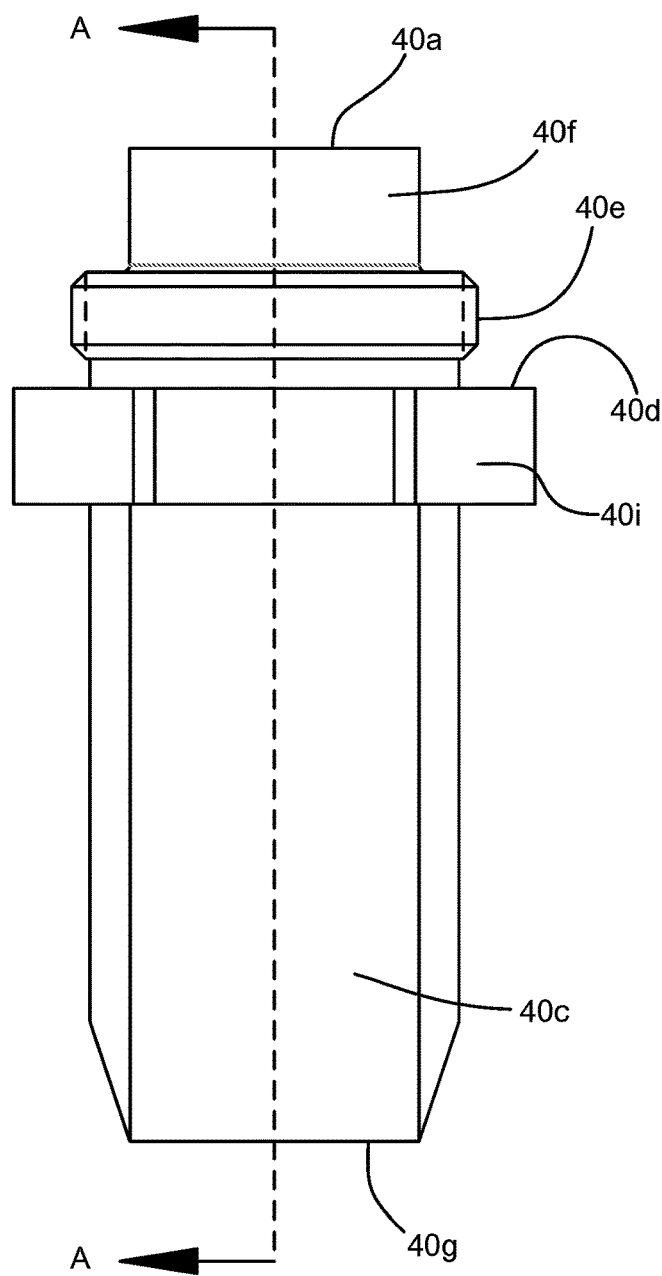
FIG. 23 is a back view of a device for removing beam energy, with cross-section assignment A-A, according to a third embodiment of the present invention.
Figure 24:
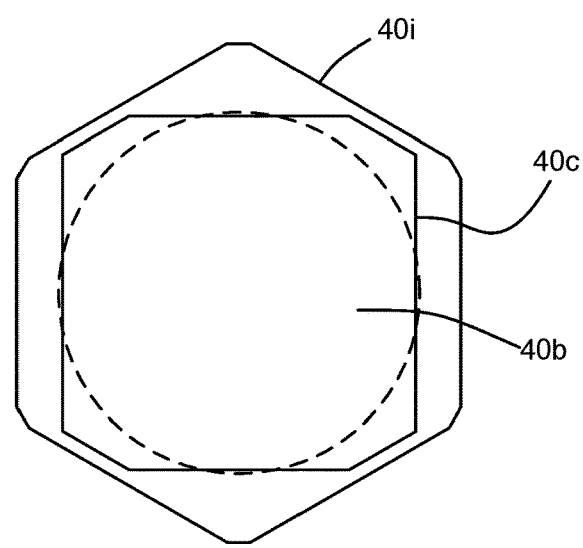
FIG. 24 is a bottom view of a device for removing beam energy according to a third embodiment of the present invention.
Figure 25:
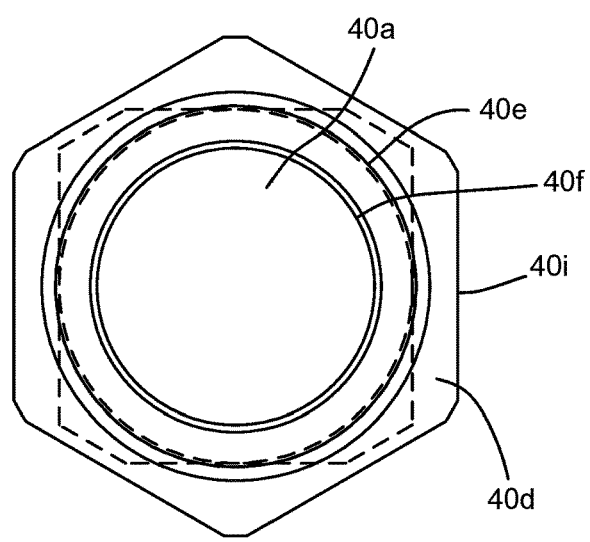
FIG. 25 is a top view of a device for removing beam energy according to a third embodiment of the present invention.

As depicted in FIG. 21, a ray 25' is illustrated to show the propagation of the energy beam within the beam dump with the line thickness representing the amount of energy in the ray with a thick line representing more energy than a thinner line. The ray 25 can propagate through the liquid sample 21 into the beam dump 30 by ingress through the optical surface 30a. The ray 25 can impinge on the first absorbing surface of revolution 30b whereupon energy may be absorbed into the energy absorbing coating in contact with first absorbing surface of revolution 30b. A ray 25a' comprising the residual energy not absorbed into energy absorbing coating at surface 30b can be directed towards the second absorbing surface of revolution 30c, whereupon energy may be absorbed into the energy absorbing coating in contact with the second energy absorbing surface of revolution 30c. A ray 25b' comprising the residual energy not absorbed into energy absorbing coating at surface 20c can be directed towards the opposing surface of the second energy absorbing surface 30c, whereupon energy may be absorbed into the energy absorbing coating in contact with the second energy absorbing surface of revolution 30c. A ray 25c' comprising unabsorbed residual energy will continue to propogate within the beam dump 30 interacting with the first or second energy absorbing surfaces 30b, 30c of revolution until all the energy may be absorbed or escapes through the optical surface 30a. For an energy absorbing material with a reflectivity of 2.1%, four incursions with the energy absorbing material can reduce an available energy to reenter the liquid sample 21 to a value less than $\frac{1}{5,000,000}$th of the original energy entering the beam dump 30, a value of which is less than that which can be distinguished from thermal noise by the turbidimeter 100.

A Third Embodiment of a Device for Removing Energy from a Beam

With reference to FIGS. 22-27, a third embodiment 40 of a device for removing a beam of energy from a liquid is illustrated. The beam dump 40 can be comprised of solid substrate selectively coated with an energy absorbing material.

The third embodiment beam dump 40 can include, but is not limited to, a solid block (or body) 40h, an optical surface 40a, a first energy absorbing planar surface 40b, a second energy absorbing faceted surface(s) 40c, a seating surface 40d, a threaded feature 40e, a cylinder feature 40f, a terminating edge 40g, and a hexagonal nut feature 40i. The solid block 40h can have a substantially right triangular shape and can be comprised of a material that will be referred to hereinafter as the substrate material.

The optical surface 40a can be adapted to be used in contact with a liquid in the turbidity measuring device 100 for an ingress of beam energy into the beam dump 40. The seating surface 40d, the threaded feature 40e, the hexagonal nut feature 40i, and the cylinder feature 40f can be implemented to attach, locate, and make a liquid tight connection between the beam dump 40 and the turbidity measuring device 100 containing the liquid sample. The energy absorbing surfaces 40b, 40c, and 40g can be coated with an energy absorbing material judicially selected from materials exhibiting low reflectivity and high absorption of wavelengths comprising the light beam. The energy absorbing coating can be in intimate contact with the substrate material of the beam dump 40, so as low a refractive difference exists between the substrate material and the energy absorbing coating. The coating applied to the surfaces 40b, 40c, and 40g can be opaque to prevent external radiation from entering the beam dump 40 by a way other than as intended through the optical surface 40a. In one embodiment, an opaque coating can be applied secondarily over the energy absorbing coating to prevent external radiation from entering the beam dump by a way other than as intended through the optical surface 40a. Generally, except for the geometric differences between the second embodiment beam dump 30 and the first embodiment beam dump 20, as well as operational differences resulting from the geometric differences, the first embodiment beam dump 20, the second embodiment beam dump 30, and the third embodiment beam dump 40 can be similar in terms of construction and operation.

Figure 26:
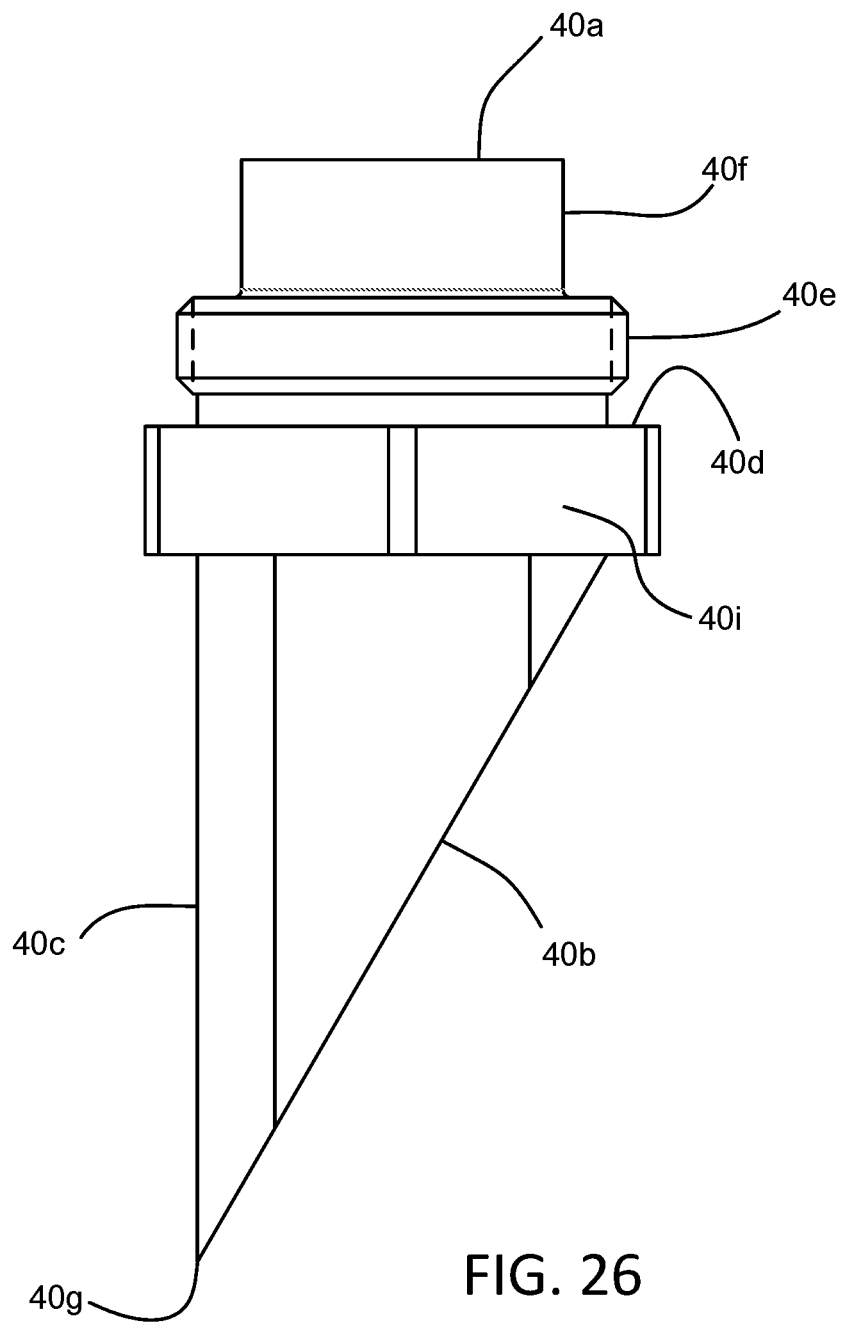
FIG. 26 is a side view of a device for removing beam energy according to a third embodiment of the present invention.
Figure 27:
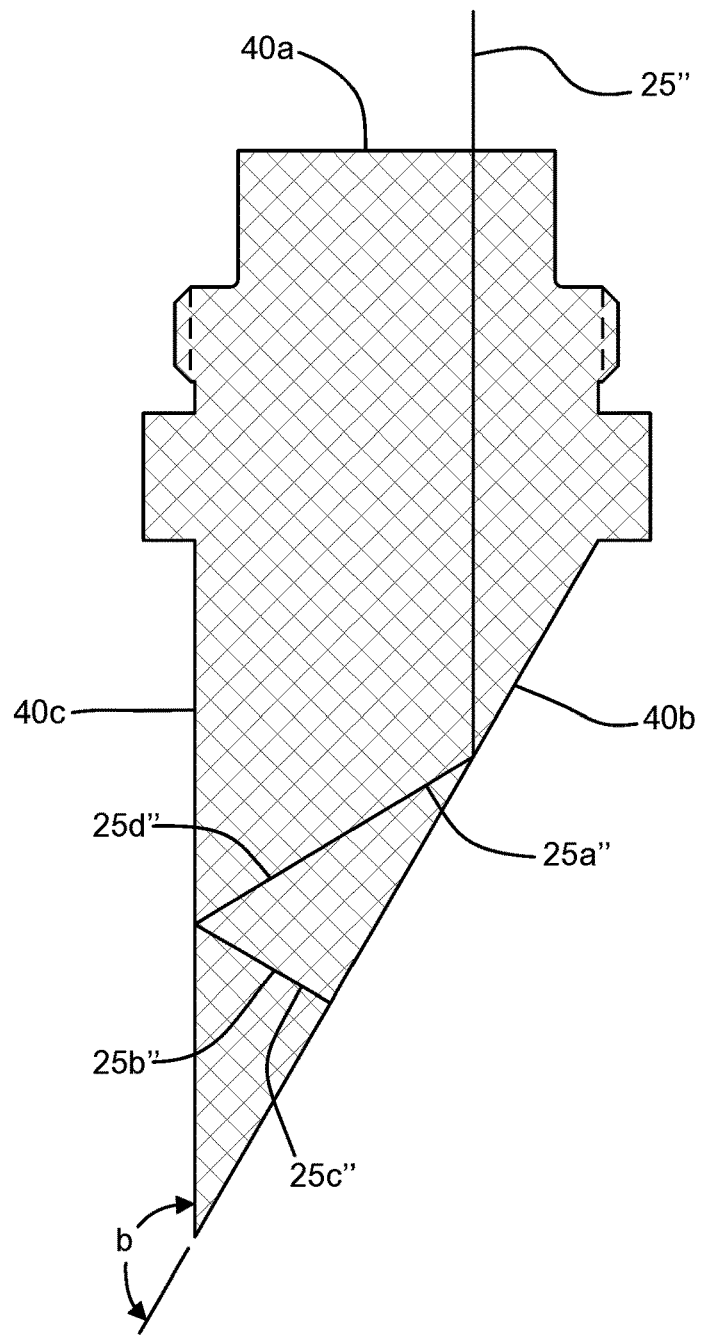
FIG. 27 is section view A-A, of FIG. 23, of a device for removing beam energy according to a third embodiment of the present invention depicting one ray path wherein energy is removed by the device.

As depicted in FIG. 27, the first energy absorbing planar surface 40b can be coincident with the second energy absorbing faceted surface 40c at the terminating edge 40g (as shown in FIG. 26) and can be inclined at an angle (b) opening towards the optical surface 40a. The incline angle (b) can approximately between 135° and 175° to provide a desirable working length for the beam dump 40 and to encourage at least three incursions of the incident beam and subsequent residuals with the energy absorbing surfaces 40b, 40c. The substrate material of the beam dump 40 can be selected from a group of materials possessing a refractive index in close match to a refractive index of the liquid sample being assayed to provide high efficiency propagation of the energy beam from the liquid sample into the beam dump 40 through the optical surface 40a. It is easily realized by those skilled in the art that various anti-reflective coatings may be applied to optical surface 40a to improve the coupling efficiency of the energy beam to the beam dump 40.

As depicted in FIG. 27, a ray 25″ is illustrated to show the propagation of the energy beam within the beam dump 40 with the line thickness representing the amount of energy in the ray with a thick line representing more energy than a thinner line. The ray 25″ can propagate through liquid sample 21 into the beam dump 40 by ingress through the optical surface 40a. The ray 25″ can impinge on the first absorbing planar surface 40b whereupon energy may be absorbed into the energy absorbing coating in contact with the first energy absorbing planar surface 40b. A ray 25a″ comprising the residual energy not absorbed into the energy absorbing coating at surface 40b can be directed towards the second energy absorbing faceted surface 40c, whereupon energy may be absorbed into the energy absorbing coating in contact with the second energy absorbing faceted surface 40c. A ray 25b″ comprising the residual energy not absorbed into the energy absorbing coating at surface 40c can be directed towards the first energy absorbing planar surface 40b, whereupon energy may be absorbed into the energy absorbing coating in contact with the first energy absorbing planar surface 40b. When the angle (b) is preferentially selected as 150°, the residual ray 25b″ may fall incident on the energy absorbing planar surface 40b substantially perpendicular to the surface 40b. A ray 25c″ comprising the residual energy not absorbed into energy absorbing coating at surface 40b can be retro-directed towards the energy absorbing faceted surface 40c. A ray 25d comprising the residual energy not absorbed into energy absorbing coating at surface 40c can be retro-directed along a ray path of the ray 25a″ towards the energy absorbing planar surface 40b. For an energy absorbing material with a reflectivity of 4%, five incursions with the energy absorbing material reduces an available energy to reenter the liquid sample 21 along the ray path 25″ to a value less than $\frac{1}{9,765,000}$th of the original energy entering the beam dump.

A Fourth Embodiment of a Device for Removing Energy from a Beam

With reference to FIGS. 28-33, a fourth embodiment 50 of a device for removing a beam of energy from a liquid is illustrated. The beam dump 50 can be comprised of a solid substrate selectively coated with an energy absorbing material.

Figure 28:
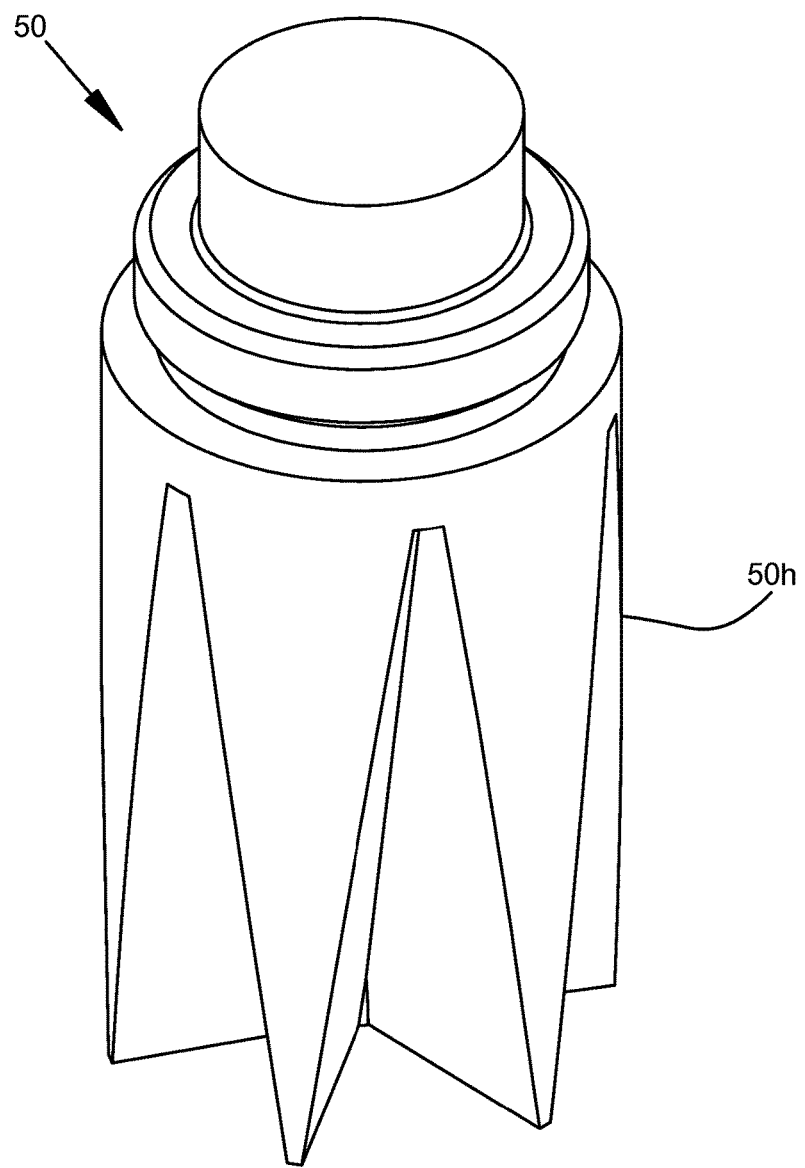
FIG. 28 is an isometric view of a device for removing beam energy according to fourth embodiment of the present invention.
Figure 29:
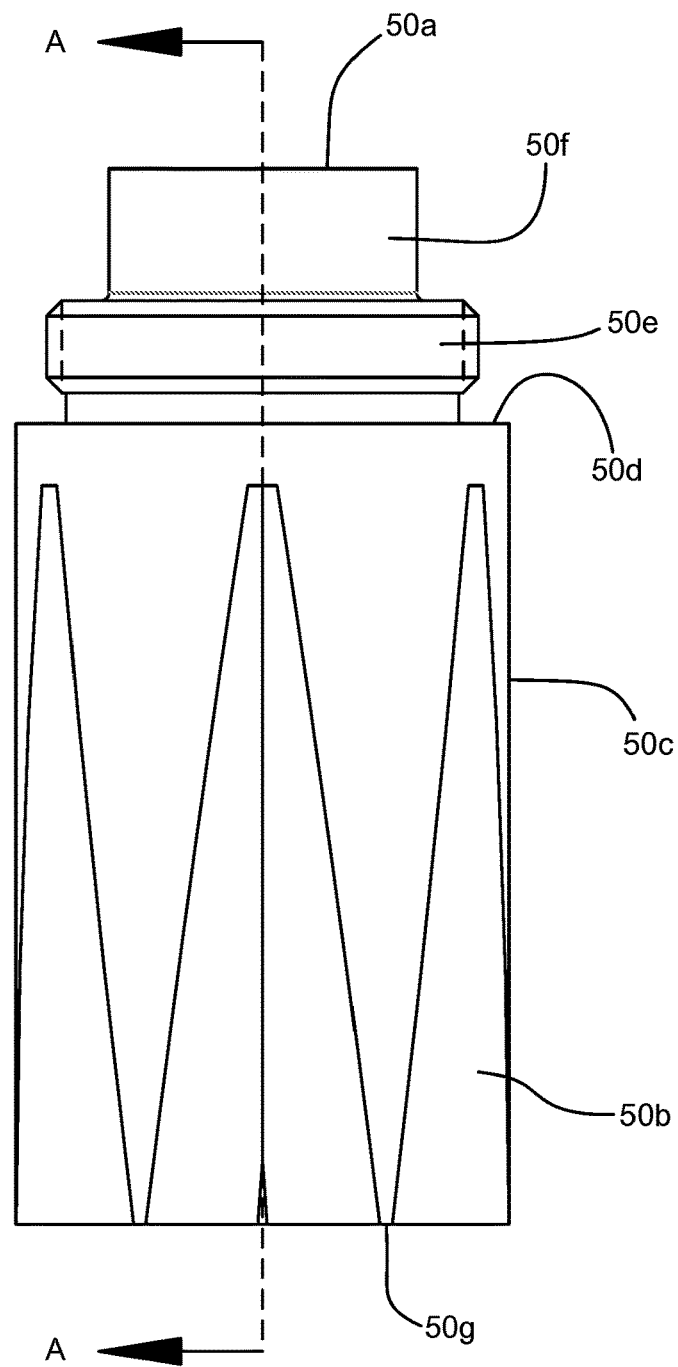
FIG. 29 is a front view of a device for removing beam energy, with cross-section assignment A-A, according to a fourth embodiment of the present invention.
Figure 30:
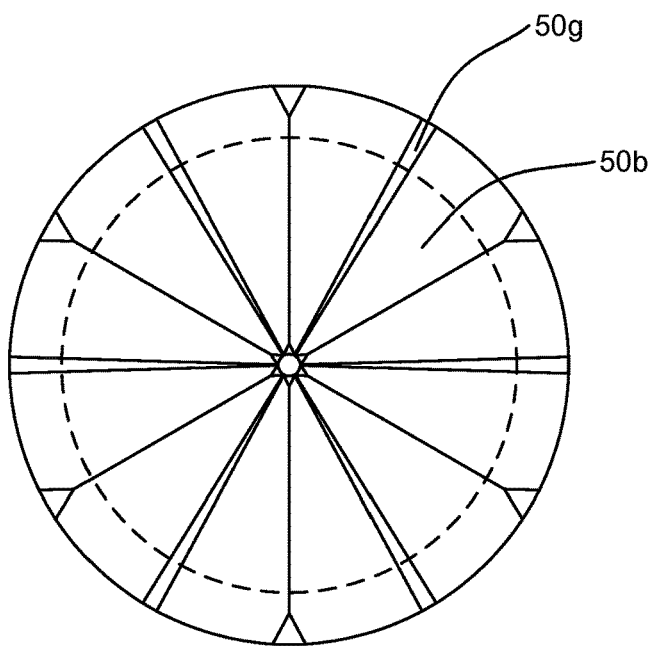
FIG. 30 is a bottom view of a device for removing beam energy according to a fourth embodiment of the present invention.
Figure 31:
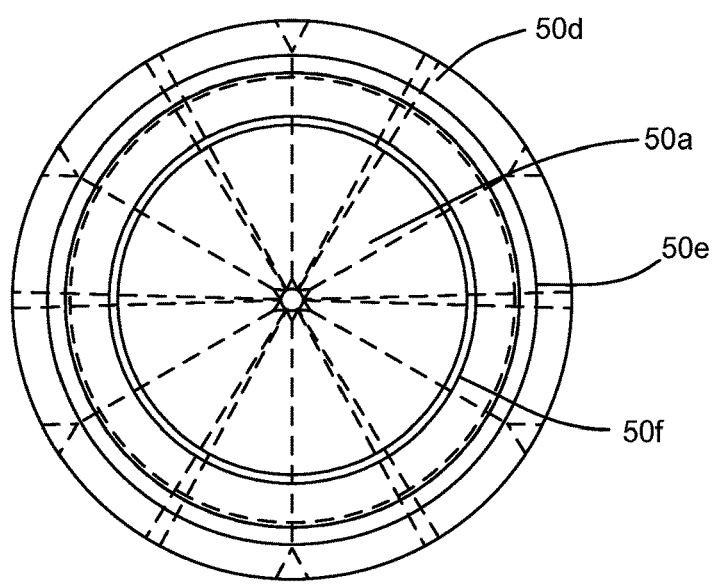
FIG. 31 is a top view of a device for removing beam energy according to a fourth embodiment of the present invention.

In one embodiment, the fourth embodiment beam dump 50 can include, but is not limited to, a solid block (or body) 50h, an optical surface 50a, a first energy absorbing wedge surface(s) 50b, a second energy absorbing cylinder surface 50c, a seating surface 50d, a threaded feature 50e, a cylinder feature 50f, and a terminating edge 50g. The solid block 50h can have a substantially cylindrical shape and can be comprised of a material that will be referred to hereinafter as the substrate material. As depicted in FIG. 28, the block 50h can include a plurality of wedge shapes tapering down towards a bottom of the block 50h.

The optical surface 50a can be in contact with a liquid for an egress of beam energy. The seating surface 50d, the thread feature 50e, and the cylinder feature 50f can be implemented to attach, locate, and make a liquid tight connection between the beam dump 50 and a vessel containing a liquid sample. The surfaces 50b, 50c, and 50g can be coated with an energy absorbing material judiciously selected from materials exhibiting low reflectivity to wavelengths of the associated energy/light beam. The energy absorbing coating can be in intimate contact with the substrate material of the beam dump 50, so as low a refractive difference can exist between the substrate material and the energy absorbing coating. The coating applied to the surfaces 50b, 50c, and 50g can be opaque to prevent external radiation from entering the beam dump 50 by a way other than intended through the optical surface 50a. In one embodiment, an opaque coating can be applied secondarily over the energy absorbing coating to prevent external radiation from entering the beam dump by a way other than as intended through the optical surface 50a.

Generally, except for the geometric differences between the second embodiment beam dump 30 and the first embodiment beam dump 20, as well as operational differences resulting from the geometric differences, the first embodiment beam dump 20, the second embodiment beam dump 30, the third embodiment beam dump 40, and the fourth embodiment beam dump 50 can be similar in terms of construction and operation.

Figure 32:
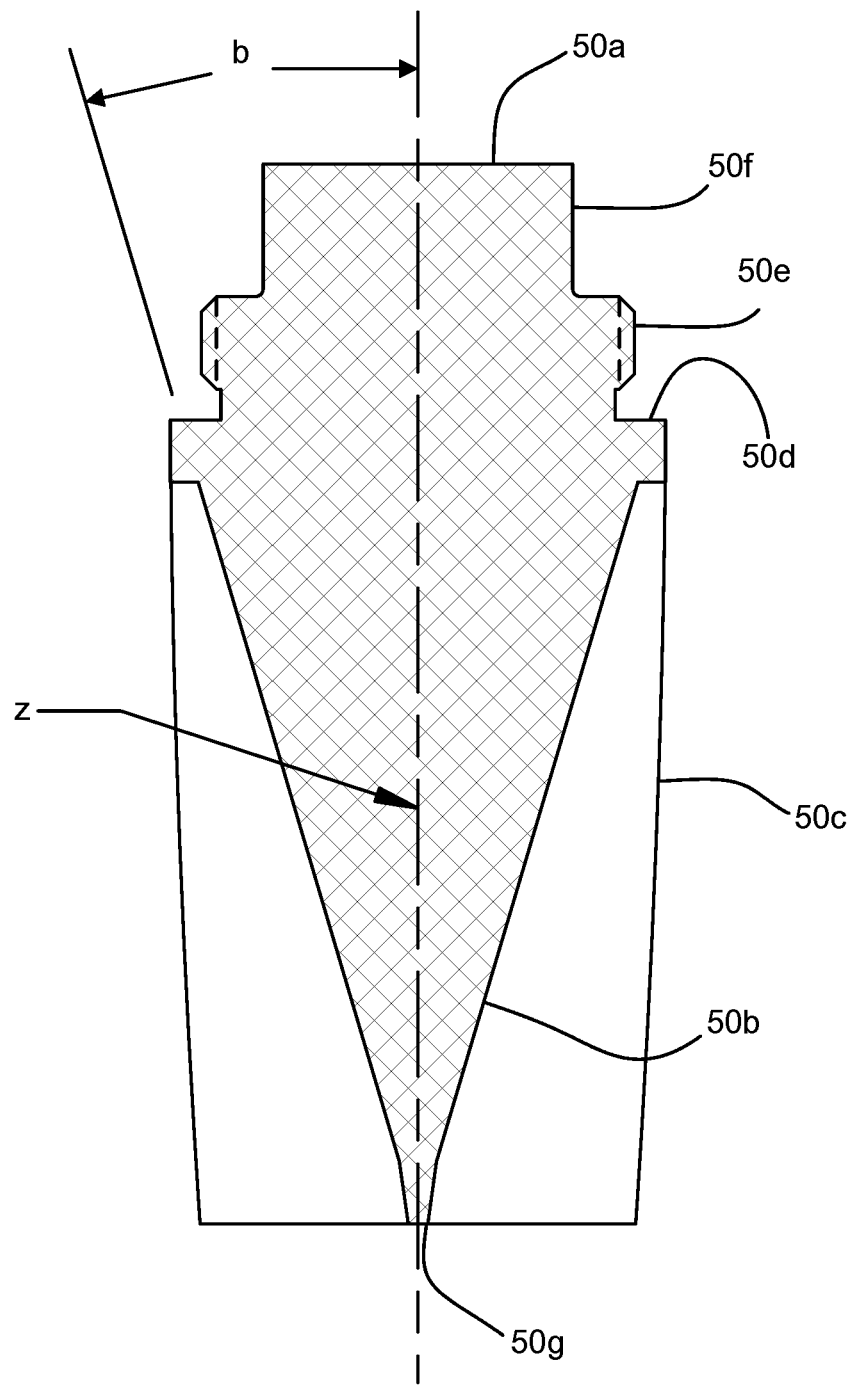
FIG. 32 is section view A-A, of FIG. 29, of a device for removing beam energy according to a fourth embodiment of the present invention.

As depicted in FIG. 32, the first energy absorbing planar surface 50b can be coincident with the second energy absorbing cylinder surface 50c at the terminating edge 50g and can be inclined at an angle (b), opening towards the optical surface 50a. The incline angle (b) can be approximately between 5° and 30° to provide sufficient working length for the beam dump 50 and to encourage at least three incursions of the incident beam and subsequent residuals with the energy absorbing surfaces 50b, 50c. The substrate material of the beam dump 50 can be selected from a material possessing a refractive index in close match to a refractive index of the liquid sample to provide high efficiency propagation of the energy beam from the liquid sample into the beam dump 50 through the optical surface 50a. It is easily realized by those skilled in the art that various anti-reflective coatings may be applied to optical surface 50a to improve the coupling efficiency of the energy beam to the beam dump.

Figure 33:
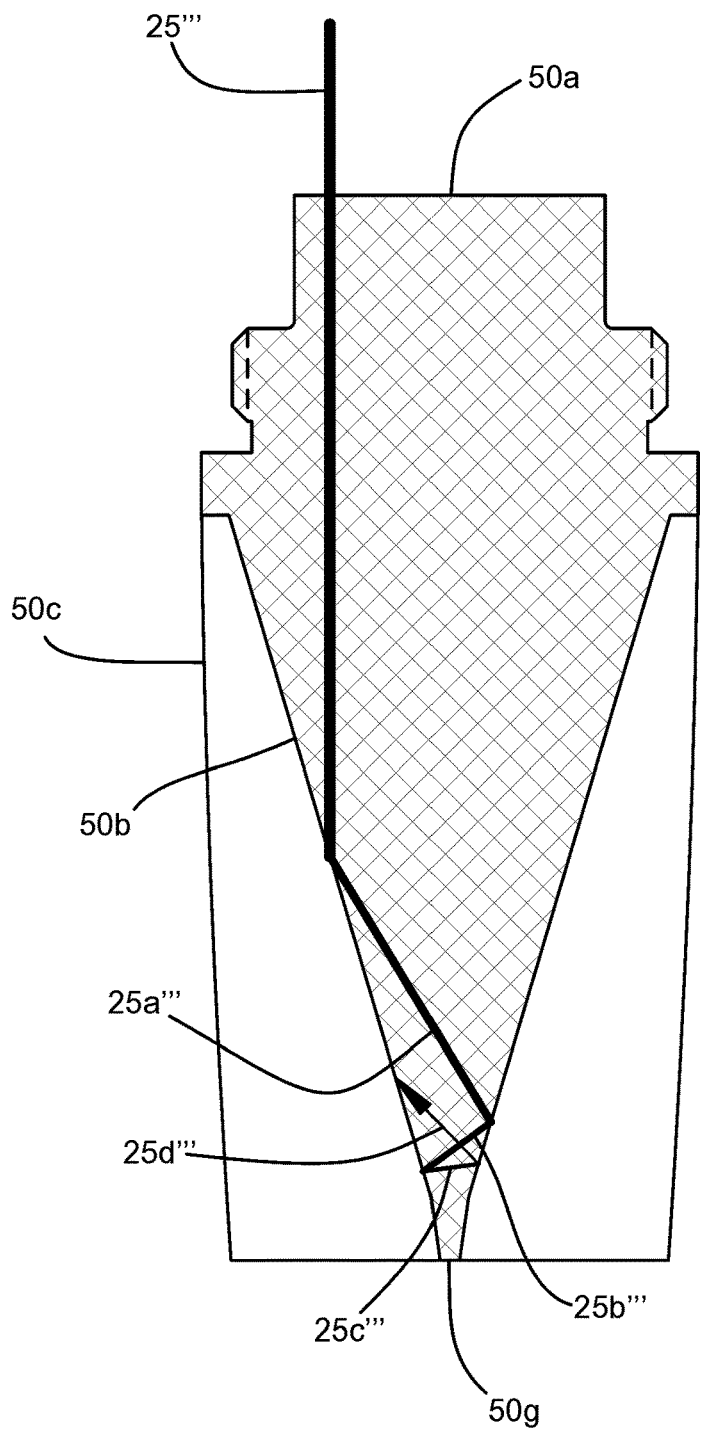
FIG. 33 is section view A-A, of FIG. 29, of a device for removing beam energy according to a fourth embodiment of the present invention depicting one ray path wherein energy is removed by the device.

As depicted in FIG. 33, a ray 25''' is illustrated to show the propagation of the energy beam within the beam dump 50 with the line thickness representing the amount of energy in the ray with a thick line representing more energy than a thinner line. The ray 25''' can propagate through the liquid sample 21 into the beam dump 50 by ingress through the optical surface 50a. The ray 25''' can impinge on the first energy absorbing wedge surface 50b whereupon energy may be absorbed into the energy absorbing coating in contact with the first energy absorbing wedge surface 50b. A ray 25a''' comprising the residual energy not absorbed into the energy absorbing coating at surface 50b can be directed downward towards an opposing first energy absorbing wedge surface 50b and outward towards the second energy absorbing cylinder surface 50c, whereupon energy may be absorbed into the energy absorbing coating in contact with the first and second energy absorbing surfaces 50b, 50c. A ray 25b''' comprising the residual energy not absorbed into the energy absorbing coating at the surfaces 50b, 50c can be directed downwards towards an opposing first energy absorbing wedge surface 40b and outward towards the second energy absorbing cylinder surface 50c, whereupon energy may be absorbed into the energy absorbing coating in contact with first and second energy absorbing surfaces 50b, 50c. A ray 25c''' comprising the residual energy not absorbed into the energy absorbing coating at the surfaces 50b, 50c can be directed upward towards an opposing first energy absorbing wedge surface 40b and inward towards a first energy absorbing wedge surface 50b, whereupon energy may be absorbed into the energy absorbing coating in contact with first energy absorbing surfaces 50b. A ray 25d''' comprising the residual energy not absorbed into the energy absorbing coating at the surfaces 50b, 50c can be directed upward towards an opposing first energy absorbing wedge surface 50b and inward towards a first energy absorbing wedge surface 50b, whereupon energy may be absorbed into the energy absorbing coating in contact with the first energy absorbing surfaces 50b. For an energy absorbing material with a reflectivity of 4%, five incursions with the material reduces the available energy to reenter the liquid sample 21 along ray path 25''' to a value less than $1/9,765,000$th of the original energy entering the beam dump 50.

A Method of Implementing a Device for Removing Energy from a Beam

A method or process of implementing one of the previously described beam dumps 20, 30, 40, 50 with the turbidity measuring device 100 is hereinafter described.

Typically, a material for the beam dump can be determined based on a refractive index of a liquid being tested by the turbidity measuring device 100. Typically, the material for the beam dump can be based on a refractive index of the liquid being tested and can be substantially similar. Other design choices can be included when choosing the material for the beam dump. For instance, a reactivity of the material with the liquid being tested can be factored in.

For a first liquid sample, a first beam dump can be selected that has a refractive index substantially similar to the first liquid sample. After a first beam dump comprising a material having a refractive index substantially similar to the refractive index of the first liquid sample has been chosen, the first beam dump can be operatively coupled to the turbidity measuring device 100. After the first beam dump has been coupled, a test can be started on the first liquid sample with the turbidity measuring device 100.

After the first test is done, a second test can be conducted on a second liquid sample. A second beam dump can be chosen for the second liquid sample based on a refractive index of the second liquid sample. For instance, the second liquid sample may have a substantially different refractive index than the first liquid sample, and a beam dump with a material having a refractive index substantially similar to the second liquid sample can be selected to use for testing. The first beam dump can be removed from the turbidity measuring device 100, and then the second beam dump can be operatively coupled to the turbidity measuring device 100. A test can then be conducted on the second liquid sample.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:
1. A device for removing energy from a beam of electromagnetic radiation, the device comprising:
    a substantially cylindrical shaped solid body configured to receive the beam of electromagnetic radiation;
    wherein the substantially cylindrical shaped body includes:
        a first surface defined by walls of the substantially cylindrical shaped solid body;
        a second surface being defined by a plurality of polygon facets forming a substantially pyramidal shape;
            wherein an apex of the second surface is located approximate a central axis of the substantially cylindrical shaped solid body; and an energy absorbing material disposed upon the first surface and the second surface.

2. The device of claim 1, wherein the device is configured to couple to a turbidity measuring device.

3. The device of claim 2, wherein the turbidity measuring device is selected from the group consisting of a turbidimeter, a fluorometer, and a nephelometer.

4. The device of claim 2, wherein the turbidity measuring device includes an electromagnetic radiation source configured to generate the beam of electromagnetic radiation.

5. The device of claim 4, wherein the beam of electromagnetic radiation is configured to strike the second energy absorbing surface first.

6. The device of claim 5, wherein energy from the beam of electromagnetic radiation not absorbed by the second energy absorbing surface is configured to deflect towards the first energy absorbing surface.

7. The device of claim 1, wherein the solid body is comprised of a material transparent to the beam of electromagnetic radiation.

8. The device of claim 1, wherein the device is manufactured from a material having a thermal conduction less than 3 W/(m·° K).

9. A device for removing energy from a beam of electromagnetic radiation, the device comprising:
a solid body removably coupled to a turbidity measuring device;
wherein the solid body includes:
   a first energy absorbing surface; and
   a second energy absorbing surface;
   wherein (i) a first portion of energy from the beam of electromagnetic radiation falling incident upon the first energy absorbing surface is absorbed, (ii) a second portion of the energy is deflected to the second energy absorbing surface, and (iii) an apex formed by the first energy absorbing surface is located approximate a central axis of the solid body.

10. The device of claim 9, wherein the turbidity measuring device includes an electromagnetic radiation source adapted to generate the beam of electromagnetic radiation.

11. The device of claim 9, wherein the first energy absorbing surface is defined by a surface of revolution.

12. The device of claim 11, wherein the second energy absorbing surface is defined by a substantially cylindrical shape.

13. The device of claim 12, wherein the second energy absorbing surface is tapered.

* * * * *